United States Patent [19]
Rabin

[11] Patent Number: 5,840,836
[45] Date of Patent: Nov. 24, 1998

[54] PANCREATIC ISLET CELL ANTIGENS OBTAINED BY MOLECULAR CLONING

[75] Inventor: Daniel U. Rabin, Branford, Conn.

[73] Assignee: Bayer Corporation, Tarrytown, N.Y.

[21] Appl. No.: 239,276

[22] Filed: May 5, 1994

Related U.S. Application Data

[63] Continuation of Ser. No. 872,646, Jun. 8, 1992, abandoned, which is a continuation of Ser. No. 715,181, Jun. 14, 1991, abandoned, which is a continuation-in-part of Ser. No. 441,703, Dec. 4, 1989, abandoned, which is a continuation-in-part of Ser. No. 312,543, Feb. 17, 1989, abandoned.

[51] Int. Cl.$^6$ .................................................. C07K 14/705
[52] U.S. Cl. .......................... 530/324; 530/325; 530/376; 530/350
[58] Field of Search ........................... 435/71, 7.21, 69.1, 435/69.3, 240.1, 252.3; 530/350, 324–328; 536/22.1, 23.4, 23.5

[56] References Cited

U.S. PATENT DOCUMENTS 5,200,318  4/1993  Rabin et al. ............................ 435/7.21

OTHER PUBLICATIONS

Srikanta et al. (1986) Mol. Biol. Med 3:113–127.

Karounos et al. (1988) Diabetes 37(5) :30A.

Moncayo et al. (1988) Diabetologia 31(7) :523A.

Glover (1984) "Principles of Cloning DNA" *Gene Cloning* pp. 1–19.

*Primary Examiner*—John Ulm
*Attorney, Agent, or Firm*—Sprung Kramer Schaefer & Briscoe

[57] ABSTRACT

Pancreatic islet cell antigens (ICA) that bind with antibodies found in the sera of patients afflicted with insulin-dependent (Type I) diabetes mellitus (IDDM). ICA proteins are expressed by recombinant cloning vehicles comprising DNA inserts isolated from islet cells. Full sequence native ICA proteins, or protein or peptide fragments thereof, can be used in the diagnosis of IDDM and in detecting or blocking human immunoglobulin, T-cells, or B-cells involved in IDDM.

26 Claims, 14 Drawing Sheets

DIABETIC

NORMAL

DIABETIC

NORMAL

DIABETIC

NORMAL

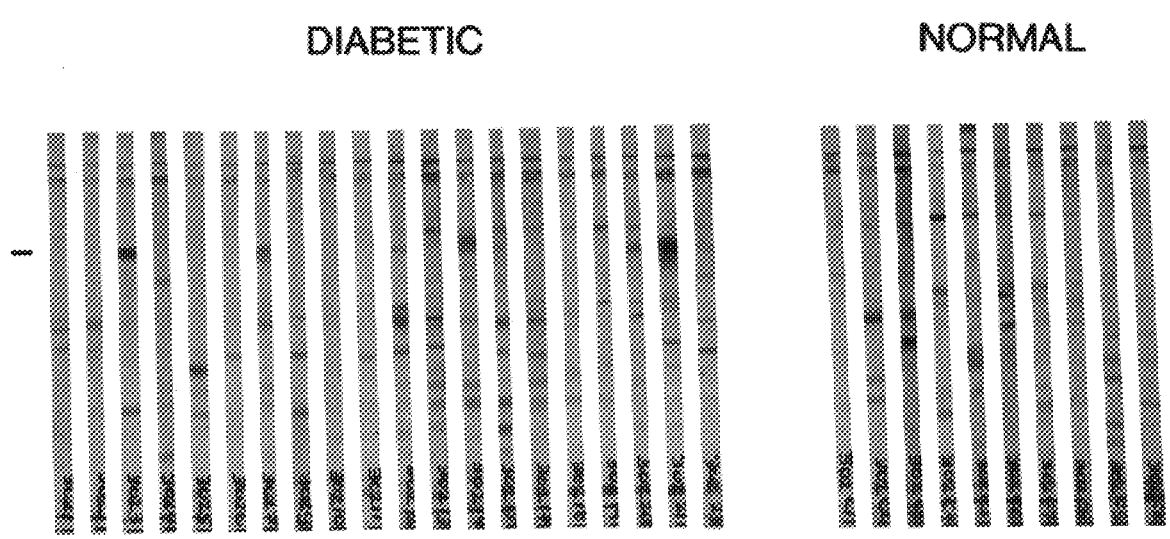
FIG. 4a  DIABETIC
FIG. 4b  NORMAL

DIABETIC

NORMAL

DIABETIC

NORMAL

ICA CLONES 2/89

| SERUM | | 12 | 13 | 208 | 302 | 313 |
|---|---|---|---|---|---|---|
| 1 | 1 | 3 | 1 | | | 1 |
| 2 | 2 | | | | | |
| 3 | 3 | | | | ? | |
| 4 | 4 | | | | | |
| 5 | 5 | 2 | | 2 | | |
| 6 | 6 | 4 | 2 | 2 | | 3 |
| 7 | 7 | 3 | | 3 | 2 | |
| 8 | 9 | | | 4 | | |
| 9 | 10 | | | | | |
| 10 | 11 | | | | | |
| 11 | 12 | 3 | 2 | | | |
| 12 | 13 | | | | | |
| 13 | 14 | | | 4 | ? | |
| 14 | 15 | | | 3 | | |
| 15 | 17 | 3 | 2 | | | 2 |
| 16 | 18 | 3 | 2 | 1 | | 1 |
| 17 | 19 | ? | | | | |
| 18 | 20 | ? | | | 2 | |
| 19 | 21 | | 1 | 1 | 4 | |
| 20 | 23 | | | | 1 | |
| 21 | c1 | | | | | |
| 22 | c2 | | | | | |
| 23 | c3 | | | | | |
| 24 | c4 | | | | | |
| 25 | c5 | | | | | |
| 26 | c6 | | | | | |
| 27 | c7 | | | | | |
| 28 | c8 | | | 2 | | |
| 29 | c9 | | | | | |
| 30 | c10 | | | | | |

FIG. 7

DIABETIC

NORMAL

DIABETIC

NORMAL

PROFILES

| SERUM | | 505 | 525 |
|---|---|---|---|
| 1 | 7601 | | 4 |
| 2 | 7645 | | |
| 3 | 7668 | | |
| 4 | 7677 | | |
| 5 | 13782 | | 4 |
| 6 | 13860 | 1 | 4 |
| 7 | 13916 | | |
| 8 | P5 | | 2 |
| 9 | P6 | 1 | |
| 10 | P7 | | 4 |
| 11 | P8 | | 3 |
| 12 | P21 | | 3 |
| 13 | P26 | 3 | |
| 14 | P28 | 2 | |
| 15 | MRC41 | | |
| 16 | MRC42 | | 1 |
| 17 | MRC43 | 1 | |
| 18 | MRC44 | | |
| 19 | MRC45 | | |
| 20 | MRC46 | | |

FIG. 10

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 1397 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GG  CCC  ATG  AAC  GCC  TTC  ATG  GTG  TGG  GCC  AAG                          32
    Pro  Met  Asn  Ala  Phe  Met  Val  Trp  Ala  Lys
                        5                        10

GAT  GAG  CGG  AGG  AAG  ATC  CTG  CAA  GCC  TTC                              62
Asp  Glu  Arg  Arg  Lys  Ile  Leu  Gln  Ala  Phe
                   15                        20

CCA  GAC  ATG  CAC  AAC  TCC  AGC  ATC  AGC  AAG                              92
Pro  Asp  Met  His  Asn  Ser  Ser  Ile  Ser  Lys
                   25                        30

ATC  CTT  GGA  TCT  CGC  TGG  AAG  TCC  ATG  ACC                              12
Ile  Leu  Gly  Ser  Arg  Trp  Lys  Ser  Met  Thr
                   35                        40

AAC  CAG  GAG  AAN  CAG  CCC  TAC  TAT  GAG  GAA                              15
Asn  Gln  Glu  Xaa  Gln  Pro  Tyr  Tyr  Glu  Glu
                   45                        50

CAG  GCT  CTG  CTG  ATC  GTC  ATC  ACC  TGG  AGA                              18
Gln  Ala  Leu  Leu  Ile  Val  Ile  Thr  Trp  Arg
                   55                        60

AGT  ATC  CTG  ACT  ACA  AGT  ACA  AGC  CGC  GGC                              21
Ser  Ile  Leu  Thr  Thr  Ser  Thr  Ser  Arg  Gly
                   65                        70

CAA  GCG  CAC  CTG  CAT  CGT  GGA  GGG  CAA  GCG                              24
Gln  Ala  His  Leu  His  Arg  Gly  Gly  Gln  Ala
                   75                        80

GCT  GCG  CGT  GGG  AGA  GTA  CAA  GGC  CCT  GAT                              27
Ala  Ala  Arg  Gly  Arg  Val  Gln  Gly  Pro  Asp
                   85                        90

GAG  GAC  CCG  GCG  TCA  GGA  TGC  CCG  CCA  GAG                              30
Glu  Asp  Pro  Ala  Ser  Gly  Cys  Pro  Pro  Glu
                   95                       100

CTA  CGT  GAT  CCC  CCC  GCA  GGC  TGG  CCA  GGT                              33
Leu  Arg  Asp  Pro  Pro  Ala  Gly  Trp  Pro  Gly
```

-continued

```
                         105                                 110
GCA GAT GAG CTC CTC AGA TGT CCT GTA CCC                                      3 6
Ala Asp Glu Leu Leu Arg Cys Pro Val Pro
                 115                             120

TCG GGC AGC AGG CAT GCC GCT GCA CAG CCA                                      3 9
Ser Gly Ser Arg His Ala Ala Ala Gln Pro
                 125                             130

CTG GTG GAG CAC TAT GTC CCT CGT AGC CTG                                      4 2
Leu Val Glu His Tyr Val Pro Arg Ser Leu
                 135                             140

GAC CCC AAC ATG CCT GTG ATC GTC AAC ACC                                      4 5
Asp Pro Asn Met Pro Val Ile Val Asn Thr
                 145                             150

TGC AGC CTC AGA GAG GAG GGT GAG GGC ACA                                      4 8
Cys Ser Leu Arg Glu Glu Gly Glu Gly Thr
                 155                             160

GAT GAC AGG CAC TCG GTG GCT GAT GGC GAG                                      5 1
Asp Asp Arg His Ser Val Ala Asp Gly Glu
                 165                             170

ATG TAC CGG TAC AGC GAG GAC GAG GAC TCG                                      5 4
Met Tyr Arg Tyr Ser Glu Asp Glu Asp Ser
                 175                             180

GAG GGT GAA GAG AAG AGC GAT GGG GAG TTG                                      5 7
Glu Gly Glu Glu Lys Ser Asp Gly Glu Leu
                 185                             190

GTG GTG CTC ACA GAC TGATCCCGGC TGGGTGGCCT                                    6 0
Val Val Leu Thr Asp
                 195

GGCCCCTTCT CCTCTGGGGA AGACCTTGTC CCAACTCGAT                                 6 4 7

GGGCACAGCC AGCCAACCTA AGACTATGTT GGTACTTGGA                                 6 8 7

CTTGTTCGTG CCCCAGAGAT GGGCAAAGCT GTGCACTTGC                                 7 2 7

AGATACATTC ATGAGGGGAG AGGCTCTCTC CCTTCCTGAG                                 7 6 7

GAGCTGTTGG CCTGGGTGGG CAGGAACTGC AGTATGGCCA                                 8 0 7

TGGGCTGAGC AGGCTGAGCA CCTCAGCCTT TAGGGCTTAT                                 8 4 7

GGCCAGGGGA CACTGTATGA CTCTCCTCTC CTGCAGGTGT                                 8 8 7

CTATCCACCT GGGGTATGGC ATCTACCGAC CTGTCTCCCT                                 9 2 7

GGGGTCACAT GCTTTGTTTC CAGGCTTGTC CTGGCTGGAC                                 9 6 7

CAGCCACTGT GGGACCAACA CCCCTCCCAC ACTCCCCAG                                1 0 0 7

ACTGCTCGTC TATCACCAGG ATCGCTTTGT ACTTTGTGCA                                1 0 4 7

AAAGGGTCTG GCTGTCCCTT GCTGTTTTCA TCTCTGCCAA                                1 0 8 7

GCCTATTGTG CCTCTGGCTG CTGTATGTGT GCGCGTGCAC                                1 1 2 7

GTGTGTGTGT TTCATCTGTT CATTCACTGC ACAGAGTATT                                1 1 6 7

TATTGTGTGC CCACTACGTG CCAGGCACTG TTGCTGAGTT                                1 2 0 7

CCTGTGGGTG TGTCTCTCGA TGCCACTCCT GCTTCTCTGG                                1 2 4 7

GGGCCTCTTT CTGTGCTTCT CTTTGTCCCC AAATTGCTAC                                1 2 8 7

CTCTTTGTCA GTCTGGGTGT CTCAGGTTCT GTGTGTCCTT                                1 3 2 7

GTGTGCATTT CTGTCTCTCT CTGTCCTCGT CTCTCTGCAA                                1 3 6 7

GGCCCTCTAT TTCTCTCTTT CTTGGTGTCT                                           1 3 9 7
```

( 2 ) INFORMATION FOR SEQ ID NO: 2:

( i ) SEQUENCE CHARACTERISTICS:
    ( A ) LENGTH: 5051 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 2:

```
GGCAGAGCTT  GAAGA  ATG  TCT  TCC  AAG  CAA                              30
                   Met  Ser  Ser  Lys  Gln
                                         5

GCC  ACC  TCT  CCA  TTT  GCC  TGT  GCA  GCT  GAT                        60
Ala  Thr  Ser  Pro  Phe  Ala  Cys  Ala  Ala  Asp
               10                             15

GGA  GAG  GAT  GCA  ATG  ACC  CAG  GAT  TTA  ACC                        90
Gly  gln  Asp  Ala  Met  Thr  Gln  Asp  Leu  Thr
               20                             25

TCA  AGG  GAA  AAG  GAA  GAG  GGC  AGT  GAT  CAA                       120
Ser  Arg  Glu  Lys  Glu  Glu  Gly  Ser  Asp  Gln
               30                             35

CAT  GTG  GCC  TCC  CAT  CTG  CCT  CTG  CAC  CCC                       150
His  Val  Ala  Ser  His  Leu  Pro  Leu  His  Pro
               40                             45

ATA  ATG  CAC  AAC  AAA  CCT  CAC  TCT  GAG  GAG                       180
Ile  Met  His  Asn  Leu  Pro  His  Ser  Glu  Glu
               50                             55

CTA  CCA  ACA  CTT  GTC  AGT  ACC  ATT  CAA  CAA                       210
Leu  Pro  Thr  Leu  Val  Ser  Thr  Ile  Gln  Gln
               60                             65

GAT  GCT  GAC  TGG  GAC  AGC  GTT  CTG  TCA  TCT                       240
Asp  Ala  Asp  Trp  Asp  Ser  Val  Leu  Ser  Ser
               70                             75

CAG  CAA  AGA  ATG  GAA  TCA  GAG  AAT  AAT  AAG                       270
Gln  Gln  Arg  Met  Glu  Ser  Gln  Asn  Asn  Lys
               80                             85

TTA  TGT  TCC  CTA  TAT  TCC  TTC  CGA  AAT  ACC                       300
Leu  Cys  Ser  Leu  Tyr  Ser  Phe  Arg  Asn  Thr
               90                             95

TCT  ACC  TCA  CCA  CAT  AAG  CCT  GAC  GAA  GGG                       330
Ser  Thr  Ser  Pro  His  Lys  Pro  Asp  Glu  Gly
              100                            105

AGT  CGG  GAC  CGT  GAG  ATA  ATG  ACC  AGT  GTT                       360
Ser  Arg  Asp  Arg  Glu  Ile  Met  Thr  Ser  Val
              110                            115

ACT  TTT  GGA  ACC  CCA  GAG  CGC  CGC  AAA  GGG                       390
Thr  Phe  Gly  Thr  Pro  Glu  Arg  Arg  Lys  Gly
              120                            125

AGT  CTT  GCC  GAT  GTG  GTG  GAC  ACA  CTG  AAA                       420
Ser  Leu  Ala  Asp  Val  Val  Asp  Thr  Leu  Lys
              130                            135

CAG  AAG  AAG  CTT  GAG  GAA  ATG  ACT  CGG  ACT                       450
Gln  Lys  Lys  Leu  Glu  Glu  Met  Thr  Arg  Thr
              140                            145

GAA  CAA  GAG  GAT  TCC  TCC  TGC  AGT  GAA  AAA                       480
Glu  Gln  Glu  Asp  Ser  Ser  Cys  Met  Glu  Lys
              150                            155

CTA  CTT  TCA  AAA  GAT  TGG  AAG  GAA  AAA  ATG                       510
Leu  Leu  Ser  Lys  Asp  Trp  Lys  Glu  Lys  Met
              160                            165

GAA  AGA  CTA  AAT  ACC  AGT  GAA  CTT  CTT  GGA                       540
Glu  Arg  Leu  Asn  Thr  Ser  Glu  Leu  Leu  Gly
              170                            175
```

```
GAA ATT AAA GGT ACA CCT GAG AGC CTG GCA                                570
Glu Ile Lys Gly Thr Pro Glu Ser Leu Ala
            180                     185

GAA AAA GAA CGG CAG CTC TCC ACC ATG ATT                                600
Glu Lys Glu Arg Gln Leu Ser Thr Met Ile
            190                     195

ACC CAG CTG ATC AGT TTA CGG GAG CAG CTA                                630
Thr Gln Leu Ile Ser Leu Arg Glu Gln Leu
            200                     205

CTG GCA GCG CAT GAT GAA AGA AAA AAA CTG                                660
Leu Ala Ala His Asp Glu Gln Lys Lys Leu
            210                     215

GCA GCG TCA CAA ATT GAG AAA CAA CGG CAG                                690
Ala Ala Ser Gln Ile Glu Lys Gln Arg Gln
            220                     225

CAA ATG GAC CTT GCT CGC CAA CAG CAA GAA                                720
Gln Met Asp Leu Ala Arg Gln Gln Gln Glu
            230                     235

CAG ATT GCG AGA CAA CAG CAG CAA CTT CTG                                750
Gln Ile Ala Arg Gln Gln Gln Gln Leu Leu
            240                     245

CAA CAG CAG CAC AAA ATT AAT CTC CTG CAG                                780
Gln Gln Gln His Lys Ile Asn Leu Leu Gln
            250                     255

CAA CAG ATC CAG GTT CAG GGT CAC ATG CCT                                810
Gln Gln Ile Gln Val Gln Gly His Met Pro
            260                     265

CCG CTC ATG ATC CCA ATT TTT CCA CAT GAC                                840
Pro Leu Met Ile Pro Ile Phe Pro His Asp
            270                     275

CAG CGG ACT CTG GCA GCA GCT GCT GCT GCC                                870
Gln Arg Thr Leu Ala Ala Ala Ala Ala Ala
            280                     285

CAA CAG GGA TTC CTC TTC CCC CCT GGA ATA                                900
Gln Gln Gly Phe Leu Phe Pro Pro Gly Ile
            290                     295

ACA TAC AAA CCA GGT GAT AAC TAC CCC GTA                                930
Thr Tyr Lys Pro Gly Asp Asn Tyr Pro Val
            300                     305

CAG TTC ATT CCA TCA ACA ATG GCA GCT GCT                                960
Gln Phe Ile Pro Ser Thr Met Ala Ala Ala
            310                     315

GCT GCT TCT GGA CTC AGC CCT TTA CAG CTC                                990
Ala Ala Ser Gly Leu Ser Pro Leu Gln Leu
            320                     325

CAG AAG GGT CAT GTC TCC CAC CCA CAA ATT                               1020
Gln Lys Gly His Val Ser His Pro Gln Ile
            330                     335

AAC CAA AGG CTA AAG GGC CTA AGT GAC CGT                               1050
Asn Gln Arg Leu Lys Gly Leu Ser Asp Arg
            340                     345

TTT GGC AGG AAT TTG GAC ACC TTT GAA CAT                               1080
Phe Gly Arg Asn Leu Asp Thr Phe Glu His
            350                     355

GGT GGT GGC CAC TCT TAC AAC CAC AAA CAG                               1110
Gly Gly Gly His Ser Tyr Asn His Lys Gln
            360                     365

ATT GAG CAG CTC TAT GCC GCT CAG CTG GCC                               1140
Ile Glu Gln Leu Tyr Ala Ala Gln Leu Ala
            370                     375
```

| | | | | | | | | | |
|---|---|---|---|---|---|---|---|---|---|
| AGC | ATG | CAG | GTG | TCA | CCT | GGA | GCA | AAG | ATG | 1170 |
| Ser | Met | Gln | Val | Ser | Pro | Gly | Ala | Lys | Met | |
| | | | | 380 | | | | | 385 | |
| CCA | TCA | ACT | CCA | CAG | CCA | CCA | AAC | ACA | GCA | 1200 |
| Pro | Ser | Thr | Pro | Gln | Pro | Pro | Asn | Thr | Ala | |
| | | | | 390 | | | | | 395 | |
| GGG | ACG | GTC | TCA | CCT | ACT | GGG | ATA | AAA | AAT | 1230 |
| Gly | Thr | Val | Ser | Pro | Thr | Gly | Ile | Lys | Asn | |
| | | | | 400 | | | | | 405 | |
| GAA | AAG | AGA | GGG | ACC | AGC | CCT | GTA | ACT | CAA | 1260 |
| Glu | Lys | Arg | Gly | Thr | Ser | Pro | Val | Thr | Gln | |
| | | | | 410 | | | | | 415 | |
| GTT | AAG | GAT | GAA | GCA | GCA | GCA | CAG | CCT | CTG | 1290 |
| Val | Lys | Asp | Glu | Ala | Ala | Ala | Gln | Pro | Leu | |
| | | | | 420 | | | | | 425 | |
| AAT | CTC | TCA | TCC | CGA | CCC | AAG | ACA | GCA | GAG | 1320 |
| Asn | Leu | Ser | Ser | Arg | Pro | Lys | Thr | Ala | Glu | |
| | | | | 430 | | | | | 435 | |
| CCT | GTA | AAG | TCC | CCA | ACG | TCT | CCC | ACC | CAG | 1350 |
| Pro | Val | Lys | Ser | Pro | Thr | Ser | Pro | Thr | Gln | |
| | | | | 440 | | | | | 445 | |
| AAC | CTC | TTC | CCA | GCC | AGC | AAA | ACC | AGC | CCT | 1380 |
| Asn | Leu | Phe | Pro | Ala | Ser | Lys | Thr | Ser | Pro | |
| | | | | 450 | | | | | 455 | |
| GTC | AAT | CTG | CCA | AAC | AAA | AGC | AGC | ATC | CCT | 1410 |
| Val | Asn | Leu | Pro | Asn | Lys | Ser | Ser | Ile | Pro | |
| | | | | 460 | | | | | 465 | |
| AGC | CCC | ATT | GGA | GGA | AGC | CTG | GGA | AGA | GGA | 1440 |
| Ser | Pro | Ile | Gly | Gly | Ser | Leu | Gly | Arg | Gly | |
| | | | | 470 | | | | | 475 | |
| TCC | TCT | TTA | GAT | ATC | CTA | TCT | AGT | CTC | AAC | 1470 |
| Ser | Ser | Leu | Asp | Ile | Leu | Ser | Ser | Leu | Asn | |
| | | | | 480 | | | | | 485 | |
| TCC | CCT | GCC | CTT | TTT | GGG | GAT | CAG | GAT | ACA | 1500 |
| Ser | Pro | Ala | Leu | Phe | Gly | Asp | Gln | Asp | Thr | |
| | | | | 490 | | | | | 495 | |
| GTG | ATG | AAA | GCC | ATT | CAG | GAG | GCG | CGG | AAG | 1530 |
| Val | Met | Lys | Ala | Ile | Gln | Glu | Ala | Arg | Lys | |
| | | | | 500 | | | | | 505 | |
| ATG | CGA | GAG | CAG | ATC | CAG | CGG | GAG | CAA | CAG | 1560 |
| Met | Arg | Glu | Gln | Ile | Gln | Arg | Glu | Gln | Gln | |
| | | | | 510 | | | | | 515 | |
| CAG | CAA | CAG | CCA | CAT | GGT | GTT | GAC | GGG | AAA | 1590 |
| Gln | Gln | Gln | Pro | His | Gly | Val | Asp | Gly | Lys | |
| | | | | 520 | | | | | 525 | |
| CTG | TCC | TCC | ATA | AAT | AAT | ATG | GGG | CTG | AAT | 1620 |
| Lys | Ser | Ser | Ile | Asn | Asn | Met | Gly | Leu | Asn | |
| | | | | 530 | | | | | 535 | |
| AGC | TGC | AGG | AAT | GAA | AAG | GAA | AGA | ACG | CGC | 1650 |
| Ser | Cys | Arg | Asn | Glu | Lys | Glu | Arg | Thr | Arg | |
| | | | | 540 | | | | | 545 | |
| TTT | GAG | AAT | TTG | GNN | CCC | CAG | TTA | ACG | GGA | 1680 |
| Phe | Glu | Asn | Leu | Xaa | Pro | Gln | Leu | Thr | Gly | |
| | | | | 550 | | | | | 555 | |
| AAG | TCA | AAT | GAA | GAT | GGA | AAA | CTG | GGC | CCA | 1710 |
| Lys | Ser | Asn | Glu | Asp | Gly | Lys | Leu | Gly | Pro | |
| | | | | 560 | | | | | 565 | |
| GGT | GTC | ATC | GAC | CTT | ACT | CGG | CCA | GAA | GAT | 1740 |
| Gly | Val | Ile | Asp | Leu | Thr | Arg | Pro | Glu | Asp | |
| | | | | 570 | | | | | 575 | |

| | | |
|---|---|---|
| GCA GAG GGA GGT GCC ACT GTG GCT GAA GCA<br>Ala Glu Gly Gly Ala Thr Val Ala Glu Ala<br>580                          585 | | 1770 |
| CGA GTC TAC AGG GAC GCC CGC GGC CTG CCA<br>Arg Val Tyr Arg Asp Ala Arg Gly Leu Pro<br>590                          595 | | 1800 |
| GCA GCG AGC CAC ACA TTA AGC GAC CAA<br>Ala Ala Ser His Thr Leu Ser Asp Gln<br>600 | | 1827 |
| TGAATGCATT CATGGTTTGG GCAAAGGATG AGAGGAGAAA | | 1867 |
| AATCCTTCAG GCCTTCCCCG ACATGCATAA CTCCAACATT | | 1907 |
| AGCAAAATCT TAGGATCTCG CTGGAAATCA ATGTCCAACC | | 1947 |
| AGGAGAAGCA ACCTTATTAT GAAGAGCAGG CCCGGCTAAG | | 1987 |
| CAAGATCCAC TTAGAGAAGT ACCCAAACTA TAAATACAAA | | 2027 |
| CCCCGACCGA AACNCACCTG CATTGTTGAT GGCAAAAAGC | | 2067 |
| TTCGGATTGG GGAGTATAAG CAACTGATGA GGTCTCGGAG | | 2107 |
| ACAGGAGATG AGGCAGTTCT TTACTGTGGG GCAACAGCCT | | 2147 |
| CAGATTCCAA TCACCACAGG AACAGGTGTT GTGTATCCTG | | 2187 |
| GTGCTATCAC TATGGCAACT ACCACACCAT CGCCTCAGAT | | 2227 |
| GACATCTGAC TGCTCTAGCA CCTCGGCCAG CGCGGAGCCC | | 2267 |
| AGCCTCCCGG TCATCCAGAG CACTTATGGT ATGAAGACAG | | 2307 |
| ATGGCGGAAG CTAGCTGGAA ATGAAATGAT CAATGGAGAG | | 2347 |
| GATGAAATGG AAATGTATGA TGACTATGAA GATGACCCCA | | 2387 |
| AATCAGACTA TAGCAGTGAA AATGAAGCCC CGGAGGCTGT | | 2427 |
| CAGAGCCAAC TGAGGAGTTT TTGTTTGCTG AATTAAAGTA | | 2467 |
| CTCTGACATT TCACCCCCCT CCCCAACAAA GAGTTATCCA | | 2507 |
| AGAGCCCGCA TGCATTTGTG GCTCCACAAT TACATCAGCA | | 2547 |
| GAATGGTCTT AATTGTTTCG TAAAGTGTGA GACAGATTAA | | 2587 |
| GTTTTCCCTG ATTTTCATG AACTTGAGTT TTTTGTTGTT | | 2627 |
| ATTGTTATTG TTGTTGTTGT TGTTTTTTT TTTTGTTGTT | | 2667 |
| ATTGTTATTG TTGTTGTTGT TGTTTTTTA ATTTAGGTGA | | 2707 |
| AGACATATTA AATATGAGAC ACCAGGACTT GAAACTTATC | | 2747 |
| TCAACCCGTA GATGTCTTAC AAGTCTTATA TTTTTGTCTT | | 2787 |
| ACTTTTTTTT TCTTTTGGAT GTTGATAAAG GTTTAAGTTA | | 2827 |
| CTGTTTTAGA TGGGGTTAAA CATTCTCACT CAGGTATGCT | | 2867 |
| GTGCCGGCCT ACAGGTTGTG AATGTGTTTT TTATTCTGAA | | 2907 |
| TTATTTAGA AAACAACTGA GGATTTCATA TTGTGAAACA | | 2947 |
| GGACAAGTCC ACGGCGTGTG CAGCTGCATG TAGAGCATAT | | 2987 |
| TCAAAAGGCC TCGGAATTCC AATTTTCCAT TTGTAGAGTT | | 3027 |
| AAACTTTGAA TGTGCCAAAC TTTTTCGTAA CTTTTGAATC | | 3067 |
| TTAATATTTT GAAAGTCTTA AAGGAGACAC TGCAAAGTCT | | 3107 |
| TAGACAATCT TTGGCATCTT AAAATAAAAT AGCAAACCAA | | 3147 |
| CATTTTTTTT TCCAGAAAAT GGTAAGGTAC TCAGGAATCT | | 3187 |

```
GGAGACAAGA TATTGTAAGG AATGAACAAG GTTGCCACAG                    3227
TGCATGGACC CAATTGTGTT TGCCTGTTGA CGTGCCATCA                    3267
GTGCGTGATG TGGTATGACA TACACACACC AGAGCAACCG                    3307
CCACACCAGA TATCGACAGA GTGGTCTTCT CTGCCTGAGA                    3347
CCACCTCTCA CTACATCCAT TATCCCTTTG CCTTTAACCC                    3387
TGACATTCAG TCTTAACACA TTTTATCTTA AATAATTTAT                    3427
TCATTCCAGA ATGTCAAGGG TCCACTTGCT ATTTATTTTT                    3467
TTTCAATTGT TGGTGCATTA ATTTAATAAT TCTTGTTTTT                    3507
CACCTTCCTT CCCCGAAGAA CTTTTCCGTC CTTTTCACCT                    3547
CCTTCTCCTG TGTACATAGT GATTTTATGT CCCCAGAACG                    3587
CCTGGAAGCA TTTCTGAAAC CAAGATATTA TTAAAAACCT                    3627
ATTATTGTTT TTAATCATGA GTATGTATCT GGCTGCAGGG                    3667
CTGTGTATTG GGATATAGGT ATATAGTCTT ACACTTAAAC                    3707
AGGTATGCCC CTGAGGTTCA CTGTGACCTC AAGTCTTTTG                    3747
CCAGAATTTT CCCCTAATTC AGTTCACAAG TGGTAGGGTC                    3787
TGCATCAGTG GCATTTCCCC CTGAATTCCA TTCAGCAGCA                    3827
AGGTTCAACA GTGGTGACTG CCAGGCAGGA GAGTCCTGCG                    3867
GCCAAACCTG AAGCCCAAGG CTCGTGGGCC ATGCAGGAAT                    3907
CTCAGTGAAG CTGTCATGGG CTGGCACCTT TACACTGAGT                    3947
TGCCTTGTCC CAGCTGGCAC ATCTAGGGAG TTCATTGCAA                    3987
AATCCCCAGG ATGCAAAAAG CCACATGACA GCCTCAGAGC                    4027
AAAGATGGTG GCAAATAGTC ATGATACATC TAGAGAATGA                    4067
AAGAAAACTG TAAGGGAGGA GAAGGAGGGG AATACATTCC                    4107
CTATATGGGA TGTTCCTACT GTTAACCTGT GGGAACAGAT                    4147
AGCTCCGGGG GCAGCAGATG AGTTCCTCTG GCTGACTCTA                    4187
TCTGTAGCCA CATGGGGACC TGCCTACGTG TGAACAAAAT                    4227
GAACTGCACT TATCACACAA GGATTTCTTT GAAGACATGC                    4267
TACTGGGGTG GGAAGCAGTG AGGTTTTATT CCCCATCTCC                    4307
TAACTACAGG GAGCTCTGCC ATGTCATTTT GGCCTTCCTG                    4347
AAACTAGGAC AGGTTGTCTA TCGGGGGGCT TCCCCAGAG                     4387
AGGTTTAGTG GGAGAATGTC AGTGAATGGG ATAGTTCACC                    4427
TCATGGGACA ACCCAGAATC TGATCACCAG GACATAGGAA                    4467
TGGCCCCATC AGATTTCCTG AGCCATTTTG TCACTTGGAA                    4507
GAAAATAGTG TACCTTTGTA TTTATTTAAG AGTGCTCAAG                    4547
GCCTAATAGC AATAAACAGG TCTAGCCAAG AAATTACAAG                    4587
CTATTCTGTT AGCTGGGAGT GCTCTCTATA AGCTGATTAA                    4627
GGTACTGATA GGAACTCTTT GTTATTCATG TTGGTTGGGG                    4667
ATTAGAAATT TGTTTTGTA CATTTATTTC AAATGAGGAG                     4707
GAGGTCATTT TTTCTCTCAA AAAATGAGTA TTTATTATTG                    4747
TCTTACTGAT TTCTTTGATT ATATACCTCT CCTCCTCAGT                    4787
```

```
TCACTCTTGT TTTTTTTCTT TCTCTTTGGC TTTTGCTTTT                    4827

GCTCTCTCTC ACTTCTTTCT TATTTGTTG CATTGGTAGA                     4867

GTGTTGTATG GCTAGCATTG TATTGTATGT AATTAATTTT                    4907

GCACAAAAGC AAACATTTAG CATAGTAGGT TAATTTTGTT                    4947

TGTTTTTATG ACCATGCCAA AATAATATTC TGGGCTGGTG                    4987

GAGAACAAAG GACTATTCTT TAGGACTGAA ACTTGATTTT                    5027

GCTCATAGTA AGTAAAAAAA AAAA                                     5051
```

( 2 ) INFORMATION FOR SEQ ID NO: 3:

( i ) SEQUENCE CHARACTERISTICS:
       ( A ) LENGTH: 575 nucleotides
       ( B ) TYPE: nucleic acid
       ( C ) STRANDEDNESS: single
       ( D ) TOPOLOGY: linear ( x i ) SEQUENCE DESCRIPTION: SEQ ID NO: 3:

```
AA  ATT  GAG  AAG  CTC  AAA  CTT  GAG  ATT  GAG  AAA           32
    Ile  Glu  Lys  Leu  Lys  Leu  Glu  Ile  Glu  Lys
                  5                        10

CTG  AAA  GCT  GAA  TCT  GGG  AAT  CCA  TCT  ATT               62
Leu  Lys  Ala  Glu  Ser  Gly  Asn  Pro  Ser  Ile
              15                            20

CGG  CAG  AAG  ATA  CGC  TTA  AAA  GAT  AAA  GCA               92
Arg  Gln  Lys  Ile  Arg  Leu  Lys  Asp  Lys  Ala
                  25                        30

GCA  GAT  GCC  AAA  AAA  ATT  CAG  GAT  CTG  GAG               122
Ala  Asp  Ala  Lys  Lys  Ile  Gln  Asp  Leu  Glu
              35                            40

CGA  CAA  GTT  AAG  GAA  ATG  GAA  GGG  ATT  CTG               152
Arg  Gln  Val  Lys  Glu  Met  Glu  Gly  Ile  Leu
                  45                        50

AAG  AGA  AGA  TAT  CCC  AAT  TCT  TTA  CCT  GCT               182
Lys  Arg  Arg  Tyr  Pro  Asn  Ser  Leu  Pro  Ala
              55                            60

TTA  ATA  TTG  GCT  GCA  TCA  GCA  GCT  GGT  GAT               212
Leu  Ile  Leu  Ala  Ala  Ser  Ala  Ala  Gly  Asp
                  65                        70

ACA  GTG  GAT  AAA  AAT  ACA  GTG  GAA  TTT  ATG               242
Thr  Val  Asp  Lys  Asn  Thr  Val  Glu  Phe  Met
              75                            80

GAG  AAA  AGG  ATA  AAA  AAG  CTA  GAA  GCT  GAT               272
Glu  Lys  Arg  Ile  Lys  Lys  Leu  Glu  Ala  Asp
                  85                        90

CTG  GAG  GGC  AAA  GAT  GAA  GAT  GCA  AAG  AAA               302
Leu  Glu  Gly  Lys  Asp  Glu  Asp  Ala  Lys  Lys
              95                           100

AGC  CTT  CGT  ACC  ATG  GAA  CAA  CAG  TTT  CAG               332
Ser  Leu  Arg  Thr  Met  Glu  Gln  Gln  Phe  Gln
                 105                       110

AAA  ATG  AAG  ATT  CAG  TAT  GAA  CAA  AGA  CTA               362
Lys  Met  Lys  Ile  Gln  Tyr  Glu  Gln  Arg  Leu
             115                           120

GAG  CAG  CAG  GAG  CAG  CTA  CTT  GCC  TGC  AAA               392
Glu  Gln  Gln  Glu  Gln  Leu  Leu  Ala  Cys  Lys
                 125                       130

TTG  AAT  CAA  CAT  GAC  TCT  CCC  AGA  ATT  AAA               422
Leu  Asn  Gln  His  Asp  Ser  Pro  Arg  Ile  Lys
```

```
                                135                              140
GCC  CTA  GAG  AAG  GAA  CTT  GAT  GAC  ATC  AAG                              452
Ala  Leu  Glu  Lys  Glu  Leu  Asp  Asp  Ile  Lys
                                145                              150

GAA  GCC  CAT  CAG  ATC  ACT  GTA  AGA  AAC  CTT                              482
Glu  Ala  His  Gln  Ile  Thr  Val  Arg  Asn  Leu
                                155                              160

GAA  GCC  GAA  ATA  GAC  GTT  CTT  AAA  CAT  CAG                              512
Glu  Ala  Glu  Ile  Asp  Val  Leu  Lys  His  Gln
                                165                              170

AAT  GCT  GAA  TTA  GAC  GTC  AAG  AAA  AAT  GAT                              542
Asn  Ala  Glu  Leu  Asp  Val  Lys  Lys  Asn  Asp
                                175                              180

AAA  GAT  GAT  GAA  GAT  TTT  CAG  TCT  ATA  GAA                              572
Lys  Asp  Asp  Glu  Asp  Phe  Gln  Ser  Ile  Glu
                                185                              190

TTC                                                                           575
Phe
```

( 2 ) INFORMATION FOR SEQ ID NO: 4:

( i ) SEQUENCE CHARACTERISTICS:
        ( A ) LENGTH: 794 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
GC   GAT  ACA  CCG  GGC  GTT  AAA  GTG  GGT  GAT  GAA                          32
     Asp  Thr  Pro  Cys  Val  Lys  Val  Gly  Asp  Glu
                     5                             10

GTG  GAG  GTA  ATG  GTT  GTT  GAA  AAA  GAA  GAC                               62
Val  Glu  Val  Met  Val  Val  Glu  Lys  Glu  Asp
                    15                             20

CGT  AAC  GGC  AAT  TTA  AAC  CTA  AGC  CGT  AAA                               92
Arg  Asn  Gly  Asn  Leu  Asn  Leu  Ser  Arg  Lys
                    25                             30

AGT  GCC  CGC  ATT  TTC  CGT  GCT  TGG  GAA  AGA                              122
Ser  Ala  Arg  Ile  Phe  Arg  Ala  Trp  Glu  Arg
                    35                             40

ATT  ATG  GAA  GTG  CAT  AAA  ACA  GGT  GAA  GTG                              152
Ile  Met  Glu  Val  His  Lys  Thr  Gly  Glu  Val
                    45                             50

GTT  ACA  GGT  TTG  GTT  ACC  AGC  AAA  ACA  AAA                              182
Val  Thr  Gly  Leu  Val  Thr  Ser  Lys  Thr  Lys
                    55                             60

GGT  GGC  TTG  ATT  GTA  GAT  GTT  TTC  GGT  ATG                              212
Gly  Gly  Leu  Ile  Val  Asp  Val  Phe  Gly  Met
                    65                             70

GAA  ACT  TTC  TTA  CCG  GGT  TCT  CAA  ATT  GAT                              242
Glu  Thr  Phe  Leu  Pro  Gly  Ser  Gln  Ile  Asp
                    75                             80

GTT  AAA  CCC  GTT  ACA  GAT  TAC  GAC  CAG  TTT                              272
Val  Lys  Pro  Val  Thr  Asp  Tyr  Asp  Gln  Phe
                    85                             90

GTT  GGT  AAA  ACA  ATG  GAG  TTT  AAA  GTT  GTT                              302
Val  Gly  Lys  Thr  Met  Glu  Phe  Lys  Val  Val
                    95                            100

AAG  ATT  AAC  GAA  ACA  ATT  AAG  AAT  GCT  GTT                              332
Lys  Ile  Asn  Glu  Thr  Ile  Lys  Asn  Ala  Val
                   105                            110
```

```
GTA TCT CAC AAA GCA TTA ATT GAA AGC GAT                                362
Val Ser His Lys Ala Leu Ile Glu Ser Asp
            115                 120

ATT GAA GCA CAA CGT GCT GAA ATA ATG AGC                                392
Ile Glu Ala Gln Arg Ala Glu Ile Met Ser
            125                 130

AAA TTA GAA AAA GGT CAG GTG TTA GAA GGT                                422
Lys Leu Glu Lys Gly Gln Val Leu Glu Gly
            135                 140

ACT GTT AAG AAC ATT ACA GAC TTC GGT GCA                                452
Thr Val Lys Asn Ile Thr Asp Phe Gly Ala
            145                 150

TTT ATG GAC CTT GGT GGC TTA GAC GGC TTA                                482
Phe Met Asp Leu Gly Gly Leu Asp Gly Leu
            155                 160

TTA TAC ATT ACA GAT ATT TCA TGG GGC AGA                                512
Leu Tyr Ile Thr Asp Ile Ser Trp Gly Arg
            165                 170

ATT TCT CAC CCA AGC GAA GTA TTG AAA ATG                                542
Ile Ser His Pro Ser Glu Val Leu Lys Met
            175                 180

GAT CAG AAA TTA AAT GTG GTT GTA TTA GAC                                572
Asp Gln Lys Leu Asn Val Val Val Leu Asp
            185                 190

TTT GAT GAT GAT AAA AAA CGT ATC AGC CTT                                602
Phe Asp Asp Asp Lys Lys Arg Ile Ser Leu
            195                 200

GGT TTA AAA CAA TTA ACA CCG CAT CCT TGG                                632
Gly Leu Lys Gln Leu Thr Pro His Pro Trp
            205                 210

GAA GTA TTA CCT GAA GGT TTG GCT GAA GGT                                662
Glu Val Leu Pro Glu Gly Leu Ala Glu Gly
            215                 220

GCT ATT GTA AAA GGT AAA GTG GTA AAT ATT                                692
Ala Ile Val Lys Gly Lys Val Val Asn Ile
            225                 230

GAA GAT TAC GGT GCA TTC TTA GAA ATT CAA                                722
Glu Asp Tyr Gly Ala Phe Leu Glu Ile Gln
            235                 240

CCG GGG GTT GAA GGT TTG GTT CAC GTA AGT                                752
Pro Gly Val Glu Gly Leu Val His Val Ser
            245                 250

GAA ATT ACC TGG GAA AAT ACA CCA ATC AAC                                782
Glu Ile Thr Trp Glu Asn Thr Pro Ile Asn
            255                 260

GCT AAA GAA TTC                                                        794
Ala Lys Glu Phe
```

( 2 ) INFORMATION FOR SEQ ID NO: 5:

( i ) SEQUENCE CHARACTERISTICS:
        ( A ) LENGTH: 1570 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
G  GAT GGC TCC CCC AAC ACC CCC TTC CGT AAG                              31
   Asp Gly Ser Pro Asn Thr Pro Phe Arg Lys
                    5                   10

GAC CTC ATC AGC CTG GAC TCA TCC CCA GCC                                 61
Asp Leu Ile Ser Leu Asp Ser Ser Pro Ala
```

|  |  |  |  |  |  |  |  |  |  |  |
|---|---|---|---|---|---|---|---|---|---|---|
|  |  |  |  | 15 |  |  |  | 20 |  |  |
| AAG | GAG | CGG | CTG | GAG | GAC | GGC | TGT | GTG | CAC | 91 |
| Lys | Glu | Arg | Leu | Glu | Asp | Gly | Cys | Val | His |  |
|  |  |  |  | 25 |  |  |  | 30 |  |  |
| CCA | CTG | GAG | GAA | GCC | ATG | CTG | AGC | TGC | GAC | 121 |
| Pro | Leu | Glu | Glu | Ala | Met | Leu | Ser | Cys | Asp |  |
|  |  |  |  | 35 |  |  |  | 40 |  |  |
| ATG | GAT | GGC | TCC | CGC | CAC | TTC | CCC | GAG | TCC | 151 |
| Met | Asp | Gly | Ser | Arg | His | Phe | Pro | Glu | Ser |  |
|  |  |  |  | 45 |  |  |  | 50 |  |  |
| CGA | AAC | AGC | AGC | CAC | ATC | AAG | AGG | CCC | ATG | 181 |
| Arg | Asn | Ser | Ser | His | Ile | Lys | Arg | Pro | Met |  |
|  |  |  |  | 55 |  |  |  | 60 |  |  |
| AAC | GCC | TTC | ATG | GTG | TGG | GCC | AAG | GAT | GAG | 211 |
| Asn | Ala | Phe | Met | Val | Trp | Ala | Lys | Asp | Glu |  |
|  |  |  |  | 65 |  |  |  | 70 |  |  |
| CGG | AGG | AAG | ATC | CTG | CAA | GCC | TTC | CCA | GAC | 241 |
| Arg | Arg | Lys | Ile | Leu | Gln | Ala | Phe | Pro | Asp |  |
|  |  |  |  | 75 |  |  |  | 80 |  |  |
| ATG | CAC | AAC | TCC | AGC | ATC | AGC | AAG | ATC | CTT | 271 |
| Met | His | Asn | Ser | Ser | Ile | Ser | Lys | Ile | Leu |  |
|  |  |  |  | 85 |  |  |  | 90 |  |  |
| GGA | TCT | CGC | TGG | AAG | TCC | ATG | ACC | AAC | CAG | 301 |
| Gly | Ser | Arg | Trp | Lys | Ser | Met | Thr | Asn | Gln |  |
|  |  |  |  | 95 |  |  |  | 100 |  |  |
| GAG | AAG | CAG | CCC | TAC | TAT | GAG | GAA | CAG | GCT | 331 |
| Glu | Lys | Gln | Pro | Tyr | Tyr | Glu | Glu | Gln | Ala |  |
|  |  |  |  | 105 |  |  |  | 110 |  |  |
| CTG | CTG | ATC | GTC | ATC | ACC | TGG | AGA | AGT | ATC | 361 |
| Leu | Leu | Ile | Val | Ile | Thr | Trp | Arg | Ser | Ile |  |
|  |  |  |  | 115 |  |  |  | 120 |  |  |
| CTG | ACT | ACA | AGT | ACA | AGC | CGC | GGC | CAA | GCG | 391 |
| Leu | Thr | Thr | Ser | Thr | Ser | Arg | Gly | Gln | Ala |  |
|  |  |  |  | 125 |  |  |  | 130 |  |  |
| CAC | CTG | CAT | CGT | GGA | GGG | CAA | GCG | GCT | GCG | 421 |
| His | Leu | His | Arg | Gly | Gly | Gln | Ala | Ala | Ala |  |
|  |  |  |  | 135 |  |  |  | 140 |  |  |
| CGT | GGG | AGA | GTA | CAA | GGC | CCT | GAT | GAG | GAC | 451 |
| Arg | Gly | Arg | Val | Gln | Gly | Pro | Asp | Glu | Asp |  |
|  |  |  |  | 145 |  |  |  | 150 |  |  |
| CCG | GCG | TCA | GGA | TGC | CCG | CCA | GAG | CTA | CGT | 481 |
| Pro | Ala | Ser | Gly | Cys | Pro | Pro | Glu | Leu | Arg |  |
|  |  |  |  | 155 |  |  |  | 160 |  |  |
| GAT | CCC | CCC | GCA | GGC | TGG | CCA | GGT | GCA | GAT | 511 |
| Asp | Pro | Pro | Ala | Gly | Trp | Pro | Gly | Ala | Asp |  |
|  |  |  |  | 165 |  |  |  | 170 |  |  |
| GAG | CTC | CTC | AGA | TGT | CCT | GTA | CCC | TCG | GGC | 541 |
| Glu | Leu | Leu | Arg | Cys | Pro | Val | Pro | Ser | Gly |  |
|  |  |  |  | 175 |  |  |  | 180 |  |  |
| AGC | AGG | CAT | GCC | GCT | GCA | CAG | CCA | CTG | GTG | 571 |
| Ser | Arg | His | Ala | Ala | Ala | Gln | Pro | Leu | Val |  |
|  |  |  |  | 185 |  |  |  | 190 |  |  |
| GAG | CAC | TAT | GTC | CCT | CGT | AGC | CTG | GAC | CCC | 601 |
| Glu | His | Tyr | Val | Pro | Arg | Ser | Leu | Asp | Pro |  |
|  |  |  |  | 195 |  |  |  | 200 |  |  |
| AAC | ATG | CCT | GTG | ATC | GTC | AAC | ACC | TGC | AGC | 631 |
| Asn | Met | Pro | Val | Ile | Val | Asn | Thr | Cys | Ser |  |
|  |  |  |  | 205 |  |  |  | 210 |  |  |
| CTC | AGA | GAG | GAG | GGT | GAG | GGC | ACA | GAT | GAC | 661 |
| Leu | Arg | Glu | Glu | Gly | Glu | Gly | Thr | Asp | Asp |  |

```
                           215                        220
AGG  CAC  TCG  GTG  GCT  GAT  GGC  GAG  ATG  TAC                              691
Arg  His  Ser  Val  Ala  Asp  Gly  Glu  Met  Tyr
                           225                        230
CGG  TAC  AGC  GAG  GAC  GAG  GAC  TCG  GAG  GGT                              721
Arg  Tyr  Ser  Glu  Asp  Glu  Asp  Ser  Glu  Gly
                           235                        240
GAA  GAG  AAG  AGC  GAT  GGG  GAG  TTG  GTG  GTG                              751
Glu  Glu  Lys  Ser  Asp  Gly  Glu  Leu  Val  Val
                           245                        250
CTC  ACA  GAC  TGATCCCGGC  TGGGTGGCCT                                         780
Leu  Thr  Asp

GGCCCCTTCT  CCTCTGGGGA  AGACCTTGTC  CCAACTCGAT                                820
GGGCAAAGCT  AGCCAACCTA  AGACTATGTT  GGTACTTGGA                                860
CTTGTTCGTG  CCCCAGAGAT  GGGCAAAGCT  GTGCACTTGC                                900
AGATACATTC  ATGAGGGGAG  AGGCTCTCTC  CCTTCCTGAG                                940
GAGCTGTTGG  CCTGGGTGGG  CAGGAACTGC  AGTATGGCCA                                980
TGGGCTGAGC  AGGCTGAGCA  CCTCAGCCTT  TAGGGCTTAT                               1020
GGCCAGGGGA  CACTGTATGA  CTCTCCTCTC  CTGCAGGTGT                               1060
CTATCCACCT  GGGGTATGGC  ATCTACCGAC  CTGTCTCCCT                               1100
GGGGTCACAT  GCTTTGTTTC  CATTCTTGTC  CTGGCTGGAC                               1140
CAGCCACTGT  GGGACCAACA  CCCCTCCCAC  ACTCCCCAG                                1180
ACTGCTCGTC  TATCACCAGG  ATCGCTTTGT  ACTTTGTGCA                               1220
AAAGGGTCTG  GCTGTCCCTT  GCTGTTTTCA  TCTCTGCCAA                               1260
GCCTATTGTG  CCTCTGGCTG  CTGTATGTGT  GCGCGTGCAC                               1300
GTGTGTGTGT  TTCATCTGTT  CATTCACTGC  ACAAGATATT                               1340
TATTGAGTGC  CCACTACGTG  CCAGGCACTG  TTGCTGAGTT                               1380
CCTGTGGGTG  TGTCTCTCGA  TGCCACTCCT  GCTTCTCTGG                               1420
GGGCCTCTTT  CTGTGCTTCT  CTTTGTCCCC  AAATTGCTAC                               1460
CTCTTTGTCA  GTCTGGGTGT  CTCAGGTTCT  GTGTGTCCTT                               1500
GTGTGCATTT  CTGTCTCTCT  CTGTCCTCGT  CTCTCTGCAA                               1540
GGCCCTCTAT  TTCTCTCTTT  CTTGGTGTCT                                          1570

( 2 ) INFORMATION FOR SEQ ID NO: 6:

( i ) SEQUENCE CHARACTERISTICS:
              ( A ) LENGTH: 3243 nucleotides
              ( B ) TYPE: nucleic acid
              ( C ) STRANDEDNESS: single
              ( D ) TOPOLOGY: linear ( x i ) SEQUENCE DESCRIPTION: SEQ ID NO: 6:

CCAGAACCCA  AGAGACCAGG  AGTGTCGGAG  GCTGCCTCTG                                 40
GAAGCCAGGA  GAAGCTGGAC  TTCAACCGAA  ATTTGAAAGA                                 80
AGTGGTGCCA  GCCATAGAGA  AGCTGTTGTC  CAGTGACTGG                                120
AAGGAGAGGT  TTCTAGGAAG  GAACTCTATG  GAAGCCAAAG                                160
ATGTCAAAGG  GACCCAAGAG  AGCCTAGCAG  AGAAGGAGCT                                200
CCAGCTTCTG  GTCATGATTC  ACCAGCTGTC  CACCCTGCGG                                240
GACCAGCTCC  TGACAGCCCA  CTCGGAGCAG  AAGAACATGG                                280
CTGCCATGCT  GTTTGAGAAG  CAGCAGCAGC  AGATGGAGCT                                320
TGCCCGGCAG  CAGCAGGAGC  AGATTGCAAA  GCAGCAGCAG                                360
CAGCTGATTC  AGCAGCAGCA  TAAGATCAAC  CTCCTTCAGC                                400
AGCAGATCCA  GCAGGTTAAC  ATGCCTTATG  TCATGATCCC                                440
AGCCTTCCCC  CCAAGCCACC  AACCTCTGCC  TGTCACCCCT                                480
```

-continued

```
GACTCCCAGC TGGCCTTACC CATTCAGCCC ATTCCCTGCA                                520
AACCAGTGGA GTATCCGCTG CAGCTGCTGC ACAGCCCCCC                                560
TGCCCCAGTG GTGAAGAGGC CTGGGGCATG GCACCCACCA                                600
CCCCCTGCAG GAGCCCTCCC AGCCCCTGAA CCTCACAGCC                                640
AAGCCCAAGG CCCCCGAGCT GCCCAACACC TCCAGCTCCC                                680
CAAGCCTGAA G ATG AGC AGC TGT GTG CCC CGC CCC                              715
            Met Ser Ser Cys Val Pro Arg Pro
                                      5

CCC AGC CAT GGA GGC CCC ACG CGG GAC CTG                                    745
Pro Ser His Gly Gly Pro Thr Arg Asp Leu
    10                  15

CAG TCC AGC CCC CCG AGC CTG CCT CTG GGC                                    775
Gln Ser Ser Pro Pro Ser Leu Pro Leu Gly
    20                  25

TTC CTT GGT GAA GGG GAC GCT GTC ACC AAA                                    805
Phe Leu Gly Glu Gly Asp Ala Val Thr Lys
    30                  35

GCC ATC CAG GAT GCT CGG CAG CTG CTG CAC                                    835
Ala Ile Gln Asp Ala Arg Gln Leu Leu His
    40                  45

AGC CAC AGT GGG GCC TTG GAT GGC TCC CCC                                    865
Ser His Ser Gly Ala Leu Asp Gly Ser Pro
    50                  55

AAC ACC CCC TTC CGT AAG GAC CTC ATC AGC                                    895
Asn Thr Pro Phe Arg Lys Asp Leu Ile Ser
    60                  65

CTG GAC TCA TCC CCA GCC AAG GAG CGG CTG                                    925
Leu Asp Ser Ser Pro Ala Lys Glu Arg Leu
    70                  75

GAG GAC GGC TGT GTG CAC CCA CTG GAG GAA                                    955
Glu Asp Gly Cys Val His Pro Leu Glu Glu
    80                  85

GCC ATG CTG AGC TGC GAC ATG GAT GGC TCC                                    985
Ala Met Leu Ser Cys Asp Met Asp Gly Ser
    90                  95

CGC CAC TTC CCC GAG TCC CGA AAC AGC AGC                                   1015
Arg His Phe Pro Glu Ser Arg Asn Ser Ser
    100                 105

CAC ATC AAG AGG CCC ATG AAC GCC TTC ATG                                   1045
His Ile Lys Arg Pro Met Asn Ala Phe Met
    110                 115

GTG TGG GCC AAG GAT GAG CGG AGG AAG ATC                                   1075
Val Trp Ala Lys Asp Glu Arg Arg Lys Ile
    120                 125

CTG CAA GCC TTC CCA GAC ATG CAC AAC TCC                                   1105
Leu Gln Ala Phe Pro Asp Met His Asn Ser
    130                 135

AGC ATC AGC AAG ATC CTT GGA TCT CGC TGG                                   1135
Ser Ile Ser Lys Ile Leu Gly Ser Arg Trp
    140                 145

AAG TCC ATG ACC AAC CAG GAG AAG CAG CCC                                   1165
Lys Ser Met Thr Asn Gln Glu Lys Gln Pro
    150                 155

TAC TAT GAG GAA CAG GCG CGG CTG AGC CGG                                   1195
Tyr Tyr Glu Glu Gln Ala Arg Leu Ser Arg
    160                 165

CAG CAC CTG GAG AAG TAT CCT GAC TAC AAG                                   1225
Gln His Leu Glu Lys Tyr Pro Asp Tyr Lys
    170                 175

TAC AAG CCG CGG CCC AAG CGC ACC TGC ATC                                   1255
Tyr Lys Pro Arg Pro Lys Arg Thr Cys Ile
    180                 185
```

| | |
|---|---|
| GTG GAG GGC AAG CGG CTG CGC GTG GGA GAG<br>Val Glu Gly Lys Arg Leu Arg Val Gly Glu<br>190                             195 | 1285 |
| TAC AAG GCC CTG ATG AGG ACC CGG CGT CAG<br>Tyr Lys Ala Leu Met Arg Thr Arg Arg Gln<br>200                             205 | 1315 |
| GAT GCC CGC CAG AGC TAC GTG ATC CCC CCG<br>Asp Ala Arg Gln Ser Tyr Val Ile Pro Pro<br>210                             215 | 1345 |
| CAG GCT GGC CAG GTG CAG ATG AGC TCC TCA<br>Gln Ala Gly Gln Val Gln Met Ser Ser Ser<br>220                             225 | 1375 |
| GAT GTC CTG TAC CCT CGG GCA GCA GGC ATG<br>Asp Val Leu Tyr Pro Arg Ala Ala Gly Met<br>230                             235 | 1405 |
| CCG CTG GCA CAG CCA CTG GTG GAG CAC TAT<br>Pro Leu Ala Gln Pro Leu Val Glu His Tyr<br>240                             245 | 1435 |
| GTC CCT CGT AGC CTG GAC CCC AAC ATG CCT<br>Val Pro Arg Ser Leu Asp Pro Asn Met Pro<br>250                             255 | 1465 |
| GTG ATC GTC AAC ACC TGC AGC CTC AGA GAG<br>Val Ile Val Asn Thr Cys Ser Leu Arg Glu<br>260                             265 | 1495 |
| GAG GGT GAG GGC ACA GAT GAC AGG CAC TCG<br>Glu Gly Glu Gly Thr Asp Asp Arg His Ser<br>270                             275 | 1525 |
| GTG GCT GAT GGC GAG ATG TAC CGG TAC AGC<br>Val Ala Asp Gly Glu Met Tyr Arg Tyr Ser<br>280                             285 | 1555 |
| GAG GAC GAG GAC TCG GAG GGT GAA GAG AAG<br>Glu Asp Glu Asp Ser Glu Gly Glu Glu Lys<br>290                             295 | 1585 |
| AGC GAT GGG GAG TTG GTG GTG CTC ACA GAC<br>Ser Asp Gly Glu Leu Val Val Leu Thr Asp<br>300                             305 | 1615 |
| TGATCCCGGC TGGGTGGGCC TGGCCCCTTC TCCTCTGGGG | 1655 |
| AAGACCTTGT CCCAACTCGA TGGGCACAGC CAGCCAACCT | 1695 |
| AAGACTATGT TGGTACTTGG ACTTGTTCGT GCCCCAGAGA | 1735 |
| TGGGCAAAGC TGTGCACTTG CAGATACATT CATGAGGGGA | 1775 |
| GAGGCGCCCT CCCTTCCTGA GGAGCTGTTG CCTGGGTGG | 1815 |
| GCAGGAACTG CAGTATGGCC ATGGGCTGAG CAGGCTGAGC | 1855 |
| ACCTCAGCCT TTAGGGCTTA TGGCCAGGGG ACACTGTATG | 1895 |
| ACTCTCCTCT CCTGCAGGTG TCTATCCACC TGGGGTATGG | 1935 |
| CATCTACCGA CCTGTCTCCC TGGGGTCACA TGCTTTGTTT | 1975 |
| CCATTCTTGT CCTGGCTGGA CCAGCCACTG TGGGACCAAC | 2015 |
| ACCCCTCCCA CACTCCCCCA GACTGCTCGT CTATCACCAG | 2055 |
| GATCGCTTTG TACTTTGTGC AAAAGGGTCT GGCTGTCCCT | 2095 |
| TGCTGTTTTC ATCTCTGCCA AGCCTATTGT GCCTCTGGCT | 2135 |
| GCTGTATGTG TGCGCGTGCA CGTGTGTGTG TTTCATCTGT | 2175 |
| TCATTCACTG CACAAGATAT TTATTGAGTG CCCACTACGT | 2215 |
| GCCAGGCACT GTTGCTGAGT TCCTGTGGGT GTGTCTCTCG | 2255 |

| | |
|---|---|
| ATGCCACTCC TGCTTCTCTG GGGGCCTCTT TCTGTGCTTC | 2295 |
| TCTTTGTCCC CAAATTGCTA CCTCTTTGTC AGTCTGGGTG | 2335 |
| TCTCAGGTTC TGTGTGTCCT TGTGTGCATT TCTGTCTCTC | 2375 |
| TCTGTCCTCG TCTCTCTGCA AGGCCCTCTA TTTCTCTCTT | 2415 |
| TCTTGGTGTC TGTCCTTTGC CCCCTGTGCC CTCTGGATTC | 2455 |
| TCTGGGTCTA TGTAGGCCCC TGGTCTGCCC TGGGCTCATC | 2495 |
| AGCCTTCCTG ACCTCCTCCT GCCCTCCCCT TCACTCCCTC | 2535 |
| CCTGGCTCTG CCAGTCGGTT CCCACGGAGC CATTTTTAGC | 2575 |
| TCTGATCAGC ATGGGAATGT GCCTCGGCCT CCAAGGGGCT | 2615 |
| TTGTCCTGGT GCCCCGCCC CTGGTCCCAA CCTGATCCCA | 2655 |
| CGAGGGAGTT GGGACAGGAG GATTGATGGT GCTCCCCTTC | 2695 |
| CTGCCAGCGT CAGAGGCCCT GGAGAGGGGC TGTCCATGGC | 2735 |
| AGCTGGTCTT TATTCCTCCC TCATGAGCAC AGGGTCGGGG | 2775 |
| GGGTCCCCAT TCTTGGAAGA GGTTGAGAAG ACTCCTGGGC | 2815 |
| TTCAGCCTCT CCCACCCAGC CCTGCCCCCT CACCTGCCTG | 2855 |
| CCCTCCCCTC CCCCCACTCT ATACTAGGGA CTGGATCTCA | 2895 |
| GCTCTGATCA GTTTCACAAA GTTTGTTCCC TAAGGAAATC | 2935 |
| AAATCCCATT GTCACCTAAC TCTGAAGATC TAAATAGCCC | 2975 |
| TTGGATCAGT ACGGGAACCC CAAATCCAC AGGGCCAGAT | 3015 |
| GTGGAGTCTG TGTCTGCCCC CGTCTTCTCT CCATCCTCAA | 3055 |
| AGCCCCCACT TCTCTCCAGG CTGTTTCTTT TTTTATGACT | 3095 |
| GTAAACATAG ATAGTGCTTT ATTTTGTTAA TAATAAGATA | 3135 |
| ATGATGAGTA ACTTAACCAG CACATTTCTC CTGTTTACAC | 3175 |
| TCGGGGATT TTTTTGTTTT CTGATGACAT AATAAAGACA | 3215 |
| GATCATTTCA GAAAAAAAAA AAAAAAA | 3243 |

( 2 ) INFORMATION FOR SEQ ID NO: 7:

( i ) SEQUENCE CHARACTERISTICS:
        ( A ) LENGTH: 2599 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

| | |
|---|---|
| GCTGCCTTCA GTCCCTAGTG TCTGGGTCCC CGCCCTCCAG | 40 |
| CCGCCTTTGA GTCGTGCCTG GGTCCTCGCC CTTGCCTCAG | 80 |
| AACCGCGAAG AAAGGAAGCT CGCGTGTTTG CTAGAAAACC | 120 |
| TAGTTGGGAG TGCGAGGCAG AGAACGTTCA GCACCTTTGT | 160 |
| TCCTCCCGAA CCCTCGGGAC AGAGGCAGGG TTCTGAGGGC | 200 |
| AGGGATTCCC CCTCGTCTTG GCCCCACCGC CCGGGCTGGG | 240 |
| CACTAAACTC GGGCCGCGGC GGGGCGAGCG AGGCGGGCTC | 280 |
| CGGAGGGAGC TGACGCCTG ATG ATG GCG CAG TCC | 314 |
|                                 Met Met Ala Gln Ser | |
|                                   5 | |

| | | | | | | | | | | |
|---|---|---|---|---|---|---|---|---|---|---|
| AAC | ATG | TTT | ACC | GTG | GCT | GAT | GTG | TTG | AGT | 344 |
| Asn | Met | Phe | Thr | Val | Ala | Asp | Val | Leu | Ser | |
| | | | 10 | | | | | | 15 | |
| CAA | GAT | GAA | CTG | CGC | AAA | AAG | CTA | TAC | CAG | 374 |
| Gln | Asp | Glu | Leu | Arg | Lys | Lys | Leu | Tyr | Gln | |
| | | | | 20 | | | | | 25 | |
| ACG | TTT | AAG | GAT | CGG | GGT | ATA | CTG | GAT | ACA | 404 |
| Thr | Phe | Lys | Asp | Arg | Gly | Ile | Leu | Asp | Thr | |
| | | | | 30 | | | | | 35 | |
| CTC | AAG | ACA | CAA | CTT | CGA | AAC | CAG | CTA | ATT | 434 |
| Leu | Lys | Thr | Gln | Leu | Arg | Asn | Gln | Leu | Ile | |
| | | | | 40 | | | | | 45 | |
| CAT | GAG | TTG | ATG | CAC | CCT | GTA | TTG | AGT | GGA | 464 |
| His | Glu | Leu | Met | His | Pro | Val | Leu | Ser | Gly | |
| | | | | 50 | | | | | 55 | |
| GAA | CTG | CAG | CCT | CGG | TCC | ATT | TCA | GTA | GAA | 494 |
| Glu | Leu | Gln | Pro | Arg | Ser | Ile | Ser | Val | Glu | |
| | | | | 60 | | | | | 65 | |
| GGG | AGC | TCC | CTC | TTA | ATA | GGC | GCC | TCT | AAC | 524 |
| Gly | Ser | Ser | Leu | Leu | Ile | Gly | Ala | Ser | Asn | |
| | | | | 70 | | | | | 75 | |
| TCT | TTA | GTG | GCA | GAT | CAC | TTA | CAA | AGA | TGT | 554 |
| Ser | Leu | Val | Ala | Asp | His | Leu | Gln | Arg | Cys | |
| | | | | 80 | | | | | 85 | |
| GGC | TAT | GAA | TAT | TCA | CTT | TCT | GTT | TTC | TTT | 584 |
| Gly | Tyr | Glu | Tyr | Ser | Leu | Ser | Val | Phe | Phe | |
| | | | | 90 | | | | | 95 | |
| CCA | GAA | AGT | GGT | TTG | GCA | AAA | GAA | AAG | GTA | 614 |
| Pro | Glu | Ser | Gly | Leu | Ala | Lys | Glu | Lys | Val | |
| | | | | 100 | | | | | 105 | |
| TTT | ACT | ATG | CAG | GAT | CTA | TTA | CAA | CTC | ATT | 644 |
| Phe | Thr | Met | Gln | Asp | Leu | Leu | Gln | Leu | Ile | |
| | | | | 110 | | | | | 115 | |
| AAA | ATC | AAC | CCT | ACT | TCC | AGT | CTC | TAC | AAA | 674 |
| Lys | Ile | Asn | Pro | Thr | Ser | Ser | Leu | Tyr | Lys | |
| | | | | 120 | | | | | 125 | |
| TCA | CTG | GTT | TCA | GGA | TCT | GAT | AAA | GAA | AAT | 704 |
| Ser | Leu | Val | Ser | Gly | Ser | Asp | Lys | Glu | Asn | |
| | | | | 130 | | | | | 135 | |
| CAA | AAA | GGT | TTT | CTT | ATG | CAT | TTT | TTA | AAA | 734 |
| Gln | Lys | Gly | Phe | Leu | Met | His | Phe | Leu | Lys | |
| | | | | 140 | | | | | 145 | |
| GAA | TTG | GCA | GAA | TAT | CAT | CAA | GCT | AAA | GAG | 764 |
| Glu | Leu | Ala | Glu | Tyr | His | Gln | Ala | Lys | Glu | |
| | | | | 150 | | | | | 155 | |
| AGT | TGT | AAT | ATG | GAA | ACT | CAG | ACA | AGT | TCG | 794 |
| Ser | Cys | Asn | Met | Glu | Thr | Gln | Thr | Ser | Ser | |
| | | | | 160 | | | | | 165 | |
| ACA | TTT | AAC | AGA | GAT | TCT | CTG | GCT | GAG | AAG | 824 |
| Thr | Phe | Asn | Arg | Asp | Ser | Leu | Ala | Glu | Lys | |
| | | | | 170 | | | | | 175 | |
| CTT | CAG | CTT | ATT | GAT | GAT | CAG | TTT | GCA | GAT | 854 |
| Leu | Gln | Leu | Ile | Asp | Asp | Gln | Phe | Ala | Asp | |
| | | | | 180 | | | | | 185 | |
| GCT | TAC | CCT | CAG | CGT | ATC | AAG | TTC | GAA | TCT | 884 |
| Ala | Tyr | Pro | Gln | Arg | Ile | Lys | Phe | Glu | Ser | |
| | | | | 190 | | | | | 195 | |
| TTA | GAA | ATA | AAG | CTA | AAT | GTG | TAT | AAG | AGA | 914 |
| Leu | Glu | Ile | Lys | Leu | Asn | Val | Tyr | Lys | Arg | |
| | | | | 200 | | | | | 205 | |

|  |  |
|---|---|
| GAA ATA GAA GAG CAA CTT CGG GCA GAA ATG<br>Glu Ile Glu Glu Gln Leu Arg Ala Glu Met<br>210                                  215 | 944 |
| TGT CAA AAG TTG AAG TTT TTT AAA GAT ACC<br>Cys Gln Lys Leu Lys Phe Phe Lys Asp Thr<br>220                                  225 | 974 |
| GAG ATA GCA AAA ATT AAA ATG GAA GCA AAA<br>Glu Ile Ala Lys Ile Lys Met Glu Ala Lys<br>230                                  235 | 1004 |
| AAA AAG TAT GAA AAG GAG TTA ACC ATG TTC<br>Lys Lys Tyr Glu Lys Glu Leu Thr Met Phe<br>240                                  245 | 1034 |
| CAG AAT GAT TTT GAA AAA GCT TGT CAA GCA<br>Gln Asn Asp Phe Glu Lys Ala Cys Gln Ala<br>250                                  255 | 1064 |
| AAA TCT GAA GCT CTC GTT CTT CGG GAA AAG<br>Lys Ser Glu Ala Leu Val Leu Arg Glu Lys<br>260                                  265 | 1094 |
| AGT ACC CTT GAA AGA ATT CAC AAG CAC CAA<br>Ser Thr Leu Glu Arg Ile His Lys His Gln<br>270                                  275 | 1124 |
| GAG ATT GAA ACA AAA GAA ATT TAT GCT CAA<br>Glu Ile Glu Thr Lys Glu Ile Tyr Ala Gln<br>280                                  285 | 1154 |
| AGG CAA CTT TTA CTA AAA GAT ATG GAT TTG<br>Arg Gln Leu Leu Leu Lys Asp Met Asp Leu<br>290                                  295 | 1184 |
| CTA AGA GGA AGA GAA GCA GAG CTG AAG CAA<br>Leu Arg Gly Arg Glu Ala Glu Leu Lys Gln<br>300                                  305 | 1214 |
| AGA GTT GAA GCT TTT GAA TTG AAC CAG AAG<br>Arg Val Glu Ala Phe Glu Leu Asn Gln Lys<br>310                                  315 | 1244 |
| CTC CAG GAA GAA AAA CAT AAA AGC ATA ACT<br>Leu Gln Glu Glu Lys Met Lys Ser Ile Thr<br>320                                  325 | 1274 |
| GAG GCA CTT AGG AGA CAG GAG CAG AAT ATA<br>Glu Ala Leu Arg Arg Gln Glu Gln Asn Ile<br>330                                  335 | 1304 |
| AAG AGT TTT GAG GAG ACC TAT GAC CGA AAG<br>Lys Ser Phe Glu Glu Thr Tyr Asp Arg Lys<br>340                                  345 | 1334 |
| CTC AAG AAT GAA CTT CTA AAG TAT CAA CTT<br>Leu Lys Asn Glu Leu Leu Lys Tyr Gln Leu<br>350                                  355 | 1364 |
| GAA CTG AAG GAT GAC TAC ATC ATT AGA ACT<br>Glu Leu Lys Asp Asp Tyr Ile Ile Arg Thr<br>360                                  365 | 1394 |
| AAT CGA CTG ATT GAA GAT GAA AGG AAG AAT<br>Asn Arg Leu Ile Glu Asp Glu Arg Lys Asn<br>370                                  375 | 1424 |
| AAA GAA AAA GCT GTT CAT TTG CAA GAG GAG<br>Lys Glu Lys Ala Val His Leu Gln Glu Glu<br>380                                  385 | 1454 |
| CTC ATA GCT ATT AAT TCA AAA AAG GAG GAA<br>Leu Ile Ala Ile Asn Ser Lys Lys Glu Glu<br>390                                  395 | 1484 |
| CTC AAT CAA TCT GTA AAT CGT GTG AAA GAA<br>Leu Asn Gln Ser Val Asn Arg Val Lys Glu<br>400                                  405 | 1514 |

```
CTT  GAG  CTT  GAA  TTA  GAG  TCT  GTC  AAA  GCC                    1544
Leu  Glu  Leu  Glu  Leu  Glu  Ser  Val  Lys  Ala
               410                           415

CAG  TCT  TTG  GCA  ATA  ACA  AAA  CAA  AAC  CAT                    1574
Gln  Ser  Leu  Ala  Ile  Thr  Lys  Gln  Asn  His
               420                           425

ATG  CTG  AAT  GAA  AAG  GTT  AAA  GAG  ATG  AGT                    1604
Met  Leu  Asn  Glu  Lys  Val  Lys  Glu  Met  Ser
               430                           435

GAT  TAT  TCA  CTA  CTA  AAA  GAA  GAG  AAA  CTG                    1634
Asp  Tyr  Ser  Leu  Leu  Lys  Glu  Glu  Lys  Leu
               440                           445

GAG  CTT  CTG  GCA  CAA  AAT  AAA  TTA  CTT  AAA                    1664
Glu  Leu  Leu  Ala  Gln  Asn  Lys  Leu  Leu  Lys
               450                           455

CAA  CAA  CTG  GAA  GAG  AGT  AGA  AAT  GAA  AAC                    1694
Gln  Gln  Leu  Glu  Glu  Ser  Arg  Asn  Glu  Asn
               460                           465

CTG  CGT  CTC  CTA  AAC  CGC  CTA  GCT  CAG  CCG                    1724
Leu  Arg  Leu  Leu  Asn  Arg  Leu  Ala  Gln  Pro
               470                           475

GCT  CCT  GAA  CTT  GCA  GTC  TTT  CAG  AAA  GAA                    1754
Ala  Pro  Glu  Leu  Ala  Val  Phe  Gln  Lys  Glu
               480                           485

CTA  CGG  AAA  GCC  GAA  AAG  GCT  ATA  GTG  GTT                    1784
Leu  Arg  Lys  Ala  Glu  Lys  Ala  Ile  Val  Val
               490                           495

GAG  CAT  GAG  GAG  TTC  GAA  AGC  TGC  AGG  CAA                    1814
Glu  His  Glu  Glu  Phe  Glu  Ser  Cys  Arg  Gln
               500                           505

GCT  CTG  CAC  AAA  CAA  CTG  CAA  GAC  GAA  ATT                    1844
Ala  Leu  His  Lys  Gln  Leu  Gln  Asp  Glu  Ile
               510                           515

GAG  CAT  TCT  GCA  CAG  CTG  AAG  GCC  CAG  ATT                    1874
Glu  His  Ser  Ala  Gln  Leu  Lys  Ala  Gln  Ile
               520                           525

CTA  GGT  TAC  AAA  GCT  TCT  GTA  AAG  AGT  TTA                    1904
Leu  Gly  Tyr  Lys  Ala  Ser  Val  Lys  Ser  Leu
               530                           535

ACT  ACT  CAG  GTT  GCC  GAT  TTA  AAA  TTG  CAA                    1934
Thr  Thr  Gln  Val  Ala  Asp  Leu  Lys  Leu  Gln
               540                           545

CTG  AAG  CAA  ACT  CAG  ACA  GCC  CTA  GAG  AAT                    1964
Leu  Lys  Gln  Thr  Gln  Thr  Ala  Leu  Glu  Asn
               550                           555

GAA  GTG  TAC  TGC  AAT  CCA  AAG  CAG  TCT  GTG                    1994
Glu  Val  Tyr  Cys  Asn  Pro  Lys  Gln  Ser  Val
               560                           565

ATC  GAT  CGT  TCT  GTC  AAT  GGA  TTA  ATA  AAT                    2024
Ile  Asp  Arg  Ser  Val  Asn  Gly  Leu  Ile  Asn
               570                           575

GGC  AAT  GTG  GTG  CCT  TGC  AAT  GGT  GAG  ATA                    2054
Gly  Asn  Val  Val  Pro  Cys  Asn  Gly  Glu  Ile
               580                           585

AGT  GGG  GAT  TTC  TTG  AAC  AAT  CCT  TTT  AAA                    2084
Ser  Gly  Asp  Phe  Leu  Asn  Asn  Pro  Phe  Lys
               590                           595

CAG  GAA  AAC  GTT  CTA  GCA  CGT  ATG  GTT  GCA                    2114
Gln  Glu  Asn  Val  Leu  Ala  Arg  Met  Val  Ala
               600                           605
```

```
TCA  AGG  ATC  ACA  AAT  TAT  CCA  ACT  GCA  TGG                                   2144
Ser  Arg  Ile  Thr  Asn  Tyr  Pro  Thr  Ala  Trp
               610                      615

GTG  GAG  GGT  AGT  TCC  CCT  GAT  TCT  GAC  CTT                                   2174
Val  Glu  Gly  Ser  Ser  Pro  Asp  Ser  Asp  Leu
               620                      625

AAT  ACT  AAG  GCA  AGG  GTC  AAA  GAG  CTT  CAG                                   2204
Asn  Thr  Lys  Ala  Arg  Val  Lys  Glu  Leu  Gln
               630                      635

CAA  GAG  GCC  GAA  CGC  TTG  GAA  AAG  GCT  TTC                                   2234
Gln  Glu  Ala  Glu  Arg  Leu  Glu  Lys  Ala  Phe
               640                      645

AGA  AGT  TAC  CAT  CGG  AGA  GTC  ATT  AAA  AAC                                   2264
Arg  Ser  Tyr  His  Arg  Arg  Val  Ile  Lys  Asn
               650                      655

TCT  GCC  AAA  AGC  CCA  CTA  GCA  GCA  AAG  AGC                                   2294
Ser  Ala  Lys  Ser  Pro  Leu  Ala  Ala  Lys  Ser
               660                      665

CCA  CCT  CTC  TGC  ACT  TGC  TGG  AAG  CCT  TCA                                   2324
Pro  Pro  Leu  Cys  Thr  Cys  Trp  Lys  Pro  Ser
               670                      675

AAA  ACA  TTA  CTT  CCA  GTT  CCC  CGG  AAA  GAC                                   2354
Lys  Thr  Leu  Leu  Pro  Val  Pro  Arg  Lys  Asp
               680                      685

ATA  TTT  TTG  GAG  AGG  ACA  GAG  TTG  TCT  CTG                                   2384
Ile  Phe  Leu  Glu  Arg  Thr  Glu  Leu  Ser  Leu
               690                      695

AGC  AGC  CTC  AAG  TGG  GCA  CAC  TTG  AAG  AAA                                   2414
Ser  Ser  Leu  Lys  Trp  Ala  His  Leu  Lys  Lys
               700                      705

GGA  ATG  ACG  TCG  TGG  AAG  CAC  TGACAGGCAG                                      2445
Gly  Met  Thr  Ser  Trp  Lys  His
               710

TGCAGCCTCG  AGGCTCCGCG  GGGGCACTTC  CTCCAGACGC                                     2485

CTCTCTTCCA  CACCCCTTCC  AAAAGCAAAA  AGAAGCCTCG                                     2525

AAAGTGAAAT  GTATCTGGAA  GGTCTGGGCA  GATCACACAT                                     2565

TGCTTCCCCC  AGTCCTTGTC  CTGACAGAAT  GCCC                                           2599
```

( 2 ) INFORMATION FOR SEQ ID NO: 8:

( i ) SEQUENCE CHARACTERISTICS:
        ( A ) LENGTH: 346 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 8:

```
TCGACCTTCG  CCTTCAATGG  GCTGGCCAGT  GGGGGAGAAC                                      40

CGGGGAGGTC  GGGGAAGAAT  CGCTTCCACT  CGGAGTGGGG                                      80

GGGCGGCTCA  CTCCAGGCGA  TACAGGCACA  GGCAAAGGAG                                     120

GGAAGCAAAC  AAGGACATAC  ATCCTGTGCT  CATACAGCCA                                     160

TGCACCATGT  ATGGGGTTTG  TCACATCACT  CGTACGCCCC                                     200

CACAAGCCTG  GAGATAGAAC  ATACCTGACT  CTAAACCCAA                                     240

GACCTCTAAC  CACCTTATGG  CGCTTTCCTG  GGAGACCCAA                                     280

TGAGGGAATG  ACATTTAAAG  CCCTCCCTAG  ACCAGAGTTC                                     320

TCAGGGTACT  TTTCTATTAA  AAAAAA                                                     346
```

( 2 ) INFORMATION FOR SEQ ID NO: 9:

( i ) SEQUENCE CHARACTERISTICS:
        ( A ) LENGTH: 1413 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 9:

```
TC  AAC  CGG  GCA  GAG  GGT  CCA  CCG  GAG  CCT  TCA                    32
    Asn  Arg  Ala  Glu  Gly  Pro  Pro  Glu  Pro  Ser
                       5                           10

CGG  GTG  AGC  AGT  GTG  TCC  TCC  CAG  TTC  AGC                        62
Arg  Val  Ser  Ser  Val  Ser  Ser  Gln  Phe  Ser
                15                            20

GAC  GCA  GCC  CAG  GCC  AGC  CCC  AGC  TCC  CAC                        92
Asp  Ala  Ala  Gln  Ala  Ser  Pro  Ser  Ser  His
                25                            30

AGC  AGC  ACC  CCG  TCC  TGG  TGC  GAG  GAG  CCG                       122
Ser  Ser  Thr  Pro  Ser  Trp  Cys  Glu  Glu  Pro
                35                            40

GCC  CAA  GCC  AAC  ATG  GAC  ATC  TCC  ACG  GGA                       152
Ala  Gln  Ala  Asn  Met  Asp  Ile  Ser  Thr  Gly
                45                            50

CAC  ATG  ATT  CTG  GCA  TAC  ATG  GAG  GAT  CAC                       182
His  Met  Ile  Leu  Ala  Tyr  Met  Glu  Asp  His
                55                            60

CTG  CGG  AAC  CGG  GAC  CGC  CTT  GCC  AAG  GAG                       212
Leu  Arg  Asn  Arg  Asp  Arg  Leu  Ala  Lys  Glu
                65                            70

TGG  CAG  GCC  CTC  TGT  GCC  TAC  CAA  GCA  GAG                       242
Trp  Gln  Ala  Leu  Cys  Ala  Tyr  Gln  Ala  Glu
                75                            80

CCA  AAC  ACC  TGT  GCC  ACC  GCG  CAG  GGG  GAG                       272
Pro  Asn  Thr  Cys  Ala  Thr  Ala  Gln  Gly  Glu
                85                            90

GGC  AAC  ATC  AAA  AAG  AAC  CGG  CAT  CCT  GAC                       302
Gly  Asn  Ile  Lys  Lys  Asn  Arg  His  Pro  Asp
                95                           100

TTC  CTG  CCC  TAT  GAC  CAT  GCC  CGC  ATA  AAA                       332
Phe  Leu  Pro  Tyr  Asp  His  Ala  Arg  Ile  Lys
               105                           110

CTG  AAG  GTG  GAG  AGC  AGC  CCT  TCT  CGG  AGC                       362
Leu  Lys  Val  Glu  Ser  Ser  Pro  Ser  Arg  Ser
               115                           120

GAT  TAC  ATC  AAC  GCC  AGC  CCC  ATT  ATT  GAG                       392
Asp  Tyr  Ile  Asn  Ala  Ser  Pro  Ile  Ile  Glu
               125                           130

CAT  GAC  CCT  CGG  ATG  CCA  GCC  TAC  ATA  GCC                       422
His  Asp  Pro  Arg  Met  Pro  Ala  Tyr  Ile  Ala
               135                           140

ACG  CAG  GGC  CCG  CTG  TCC  CAT  ACC  ATC  GCA                       452
Thr  Gln  Gly  Pro  Leu  Ser  His  Thr  Ile  Ala
               145                           150

GAC  TTC  TGG  CAG  ATG  GTG  TGG  GAG  AGC  GGC                       482
Asp  Phe  Trp  Gln  Met  Val  Trp  Glu  Ser  Gly
               155                           160

TGC  ACC  GTC  ATC  GTC  ATG  CTG  ACC  CCG  CTG                       512
Cys  Thr  Val  Ile  Val  Met  Leu  Thr  Pro  Leu
               165                           170
```

-continued

| | | | | | | | | | | |
|---|---|---|---|---|---|---|---|---|---|---|
| GTG | GAG | GAT | GGT | GTC | AAG | CAG | TGT | GAC | CGC | 542 |
| Val | Glu | Asp | Gly | Val | Lys | Gln | Cys | Asp | Arg | |
| | | | | 175 | | | | | 180 | |
| TAC | TGG | CCA | GAT | GAG | GGT | GCC | TCC | CTC | TAC | 572 |
| Tyr | Trp | Pro | Asp | Glu | Gly | Ala | Ser | Leu | Tyr | |
| | | | | 185 | | | | | 190 | |
| CAC | GTA | TAT | GAG | GTG | AAC | CTG | GTG | TCG | GAG | 602 |
| His | Val | Tyr | Glu | Val | Asn | Leu | Val | Ser | Glu | |
| | | | | 195 | | | | | 200 | |
| CAC | ATC | TGG | TGC | GAG | GAC | TTT | CTG | GTG | CGG | 632 |
| His | Ile | Trp | Cys | Glu | Asp | Phe | Leu | Val | Arg | |
| | | | | 205 | | | | | 210 | |
| AGC | TTC | TAC | CTG | AAG | AAC | GTG | CAG | ACC | CAG | 662 |
| Ser | Phe | Tyr | Leu | Lys | Asn | Val | Gln | Thr | Gln | |
| | | | | 215 | | | | | 220 | |
| GAG | ACG | CGC | ACG | CTC | ACG | CAG | TTC | CAC | TTC | 692 |
| Glu | Thr | Arg | Thr | Leu | Thr | Gln | Phe | His | Phe | |
| | | | | 225 | | | | | 230 | |
| CTC | AGC | TGG | CCG | GCA | GAG | GGC | ACA | CCG | GCC | 722 |
| Leu | Ser | Trp | Pro | Ala | Glu | Gly | Thr | Pro | Ala | |
| | | | | 235 | | | | | 240 | |
| TCC | ACG | CGG | CCC | CTG | CTG | GAC | TTC | CGC | AGG | 752 |
| Ser | Thr | Arg | Pro | Leu | Leu | Asp | Phe | Arg | Arg | |
| | | | | 245 | | | | | 250 | |
| AAG | GTG | AAC | AAG | TGC | TAC | CGG | GGC | CGC | TCC | 782 |
| Lys | Val | Asn | Lys | Cys | Tyr | Arg | Gly | Arg | Ser | |
| | | | | 255 | | | | | 260 | |
| TGC | CCC | ATC | ATC | GTG | CAC | TGC | AGT | GAT | GGT | 812 |
| Cys | Pro | Ile | Ile | Val | His | Cys | Ser | Asp | Gly | |
| | | | | 265 | | | | | 270 | |
| GCG | GGG | AGG | ACC | GGC | ACC | TAC | ATC | CTC | ATC | 842 |
| Ala | Gly | Arg | Thr | Gly | Thr | Tyr | Ile | Leu | Ile | |
| | | | | 275 | | | | | 280 | |
| GAC | ATG | GTC | CTG | AAC | CGC | ATG | GCA | AAA | GGA | 872 |
| Asp | Met | Val | Leu | Asn | Arg | Met | Ala | Lys | Gly | |
| | | | | 285 | | | | | 290 | |
| GTG | AAG | GAG | ATT | GACATCGCT | GCCACCCTGGA | | | | | 904 |
| Val | Lys | Glu | Ile | | | | | | | |

| | | | | |
|---|---|---|---|---|
| GCATGTCCGT | GACCAGCGGC | CTGGCCTTGT | CCGCTCTAAG | 944 |
| GACCAGTTTG | AATTTGCCCT | GACAGCCGTG | GCGGAGGAAG | 984 |
| TGAATGCCAT | CCTCAAGGCC | CTGCCCCAGT | GAGACCCTGG | 1024 |
| GGCCCCTTGG | CGGGCAGCCC | AGCCTCTGTC | CCTCTTTGCC | 1064 |
| TGTGTGAGCA | TCTCTGTGTA | CCCACTCCTC | ACTGCCCCAC | 1104 |
| CAGCCACCTC | TTGGGCATGC | TCAGCCCTTC | CTAGAAGAGT | 1144 |
| CAGGAAGGGA | AAGCCAGAAG | GGGCACGCCT | GCCCAGCCTC | 1184 |
| GCATGCCAGA | GCCTGGGGCA | TCCCAGAGCC | AGAGCATCC | 1224 |
| CATGGGGGTG | CTGCAGCCAG | GAGGAGAGGA | AAGGACATGG | 1264 |
| GTAGCAATTC | TACCCAGAGC | CTTCTCCTGC | CTACATTCCC | 1304 |
| TGGCCTGGCT | CTCCTGTAGC | TCTCCTGGGG | TTCTGGGAGT | 1344 |
| TCCCTGAACA | TCTGTGTGTG | TCCCCCTATG | CTCCAGTATG | 1384 |
| GAAGAATGGG | GTGGAGGGTC | GCCACACCC | | 1413 |

( 2 ) INFORMATION FOR SEQ ID NO: 10:

( i ) SEQUENCE CHARACTERISTICS:
   ( A ) LENGTH: 3311 nucleotides
   ( B ) TYPE: nucleic acid
   ( C ) STRANDEDNESS: single
   ( D ) TOPOLOGY: linear ( x i ) SEQUENCE DESCRIPTION: SEQ ID NO: 10:

```
CTCCAACGCT  TACAAGGTGT  GCTCCGACAA  CTCATGTCCC                                    40

AAGGATTGTC  CTGGCACGAT  GACCTCACCC  AGTATGTGAT                                    80

CTCTCAGGAG  ATGGAGCGCA  TCCCCAGGCT  TCGCCCCCA                                    120

GAGCCCCGTC  CAAGGGACAG  GTCTGGCTTG  GCACCCAAGA                                   160

GACCTGGTCC  TGCTGGAGAG  CTGCTTTTAC  AGGACATCCC                                   200

CACTGGCTCC  GCCCCTGCTG  CCCAGCATCG  GCTTCCACAA                                   240

CCACCAGTGG  GCAAAGGTGG  AGCTGGGGCC  AGCTCCTCTC                                   280

TGTCCCCTCT  GCAGGCTGAG  CTGCTCCCGC  CTCTCTTGGA                                   320

GCACCTGCTG  CTGCCCCCAC  AGCCTCCCCA  CCCTTCACTG                                   360

AGTTACGAAC  CTGCCTTGCT  GCAGCCCTAC  CTGTTCCACC                                   400

AGTTTGGCTC  CCGTGATGGC  TCCAGGGTCT  CAGAGGGCTC                                   440

CCCAGGGATG  GTCAGTGTCG  GCCCCCTGCC  CAAGGCTGAA                                   480

GCCCCTGCCC  TCTTCAGCAG  AACTGCCTCC  AAGGGCATAT                                   520

TTGGGGACCA  CCCTGGCCAC  TCCTACGGGG  ACCTTCCAGG                                   560

GCCTTCACCT  GCCCAGCTTT  TTCAAGACTC  TGGGCTGCTC                                   600

TATCTGGCCC  AGGAGTTGCC  AGCACCCAGC  AGGGCCAGGG                                   640

TGCCAAGGCT  GCCAGAGCAA  GGGAGCAGCA  GCCGGGCAGA                                   680

GGACTCCCCA  GAGGGCTATG  AGAAGGAAGG  ACTAGGGGAT                                   720

CGTGGAGAGA  AGCCTGCTTC  CCCAGCTGTG  CAGCCAGATG                                   760

CGGCTCTGCA  GAGGCTGGCC  GCTGTGCTGG  CGGGCTATGG                                   800

GGTAGAGCTG  CGTCAGCTGA  CCCCTGAGCA  GCTCTCCACA                                   840

CTCCTGACCC  TGCTGCAGCT  ACTGCCCAAG  GGTGCAGGAA                                   880

GAAATCCGGG  AGGGGTTGTA  AATGTTGGAG  CTGATATCAA                                   920

GAAAACA ATG GAG GGG CCG GTG GAG GGC                                              948
        Met Glu Gly Pro Val Glu Gly
        1               5

AGA GAC ACA GCA GAG CTT CCA GCC CGC ACA                                          978
Arg Asp Thr Ala Glu Leu Pro Ala Arg Thr
        10                  15

TCC CCC ATG CCT GGA CAC CCC ACT GCC AGC                                         1008
Ser Pro Met Pro Gly His Pro Thr Ala Ser
        20                  25

CCT ACC TCC AGT GAA GTC CAG CAG GTG CCA                                         1038
Pro Thr Ser Ser Glu Val Gln Gln Val Pro
        30                  35

AGC CCT GTC TCC TCT GAG CCT CCC AAA GCT                                         1068
Ser Pro Val Ser Ser Glu Pro Pro Lys Ala
        40                  45

GCC AGA CCC CCT GTG ACA CCT GTC CTG CTA                                         1098
Ala Arg Pro Pro Val Thr Pro Val Leu Leu
        50                  55

GAG AAG AAA AGC CCA CTG GGC CAG AGC CAG                                         1128
Glu Lys Lys Ser Pro Leu Gly Gln Ser Gln
```

|     |     |     |     |     |     |     |     |     |     |      |
|-----|-----|-----|-----|-----|-----|-----|-----|-----|-----|------|
|     |     | 60  |     |     |     |     | 65  |     |     |      |
| CCC | ACG | GTG | GCA | GGA | CAG | CCC | TCA | GCC | CGC | 1158 |
| Pro | Thr | Val | Ala | Gly | Gln | Pro | Ser | Ala | Arg |      |
|     |     | 70  |     |     |     |     | 75  |     |     |      |
| CCA | GCA | GCA | GAG | GAA | TAT | GGC | TAC | ATC | GTC | 1188 |
| Pro | Ala | Ala | Glu | Glu | Tyr | Gly | Tyr | Ile | Val |      |
|     |     | 80  |     |     |     |     | 85  |     |     |      |
| ACT | GAT | CAG | AAG | CCC | CTG | AGC | CTG | GCT | GCA | 1218 |
| Thr | Asp | Gln | Lys | Pro | Leu | Ser | Leu | Ala | Ala |      |
|     |     | 90  |     |     |     |     | 95  |     |     |      |
| GGA | GTG | AAG | CTG | CTG | GAG | ATC | CTG | GCT | GAG | 1248 |
| Gly | Val | Lys | Leu | Leu | Glu | Ile | Leu | Ala | Glu |      |
|     |     | 100 |     |     |     |     | 105 |     |     |      |
| CAT | GTG | CAC | ATG | TCC | TCA | GGC | AGC | TTC | ATC | 1278 |
| His | Val | His | Met | Ser | Ser | Gly | Ser | Phe | Ile |      |
|     |     | 110 |     |     |     |     | 115 |     |     |      |
| AAC | ATC | AGT | GTG | GTG | GGA | CCA | GCC | CTC | ACC | 1308 |
| Asn | Ile | Ser | Val | Val | Gly | Pro | Ala | Leu | Thr |      |
|     |     | 120 |     |     |     |     | 125 |     |     |      |
| TTC | CGC | ATC | CGG | CAC | AAT | GAG | CAG | AAC | CTG | 1338 |
| Phe | Arg | Ile | Arg | His | Asn | Glu | Gln | asn | Leu |      |
|     |     | 130 |     |     |     |     | 135 |     |     |      |
| TCT | TTG | GCT | GAT | GTG | ACC | CAA | CAA | GCA | GGG | 1368 |
| Ser | Leu | Ala | Asp | Val | Thr | Gln | Gln | Ala | Gly |      |
|     |     | 140 |     |     |     |     | 145 |     |     |      |
| CTG | GTG | AAG | TCT | GAA | CTG | GAA | GCA | CAG | ACA | 1398 |
| Leu | Val | Lys | Ser | Glu | Leu | Glu | Ala | Gln | Thr |      |
|     |     | 150 |     |     |     |     | 155 |     |     |      |
| GGG | CTC | CAA | ATC | TTG | CAG | ACA | GGA | GTG | GGA | 1428 |
| Gly | Leu | Gln | Ile | Leu | Gln | Thr | Gly | Val | Gly |      |
|     |     | 160 |     |     |     |     | 165 |     |     |      |
| CAG | AGG | GAG | GAG | GCA | GCT | GCA | GTC | CTT | CCC | 1458 |
| Gln | Arg | Glu | Glu | Ala | Ala | Ala | Val | Leu | Pro |      |
|     |     | 170 |     |     |     |     | 175 |     |     |      |
| CAA | ACT | GCG | CAC | AGC | ACC | TCA | CCC | ATG | CGC | 1488 |
| Gln | Thr | Ala | His | Ser | Thr | Ser | Pro | Met | Arg |      |
|     |     | 180 |     |     |     |     | 185 |     |     |      |
| TCA | GTG | CTG | CTC | ACT | CTG | GTG | GCC | CTG | GCA | 1518 |
| Ser | Val | Leu | Leu | Thr | Leu | Val | Ala | Leu | Ala |      |
|     |     | 190 |     |     |     |     | 195 |     |     |      |
| GGT | GTG | GCT | GGG | CTG | CTG | GTG | GCT | CTG | GCT | 1548 |
| Gly | Val | Ala | Gly | Leu | Leu | Val | Ala | Leu | Ala |      |
|     |     | 200 |     |     |     |     | 205 |     |     |      |
| GTG | GCT | CTG | TGT | GTG | CGG | CAG | CAT | GCG | CGG | 1578 |
| Val | Ala | Leu | Cys | Val | Arg | Gln | His | Ala | Arg |      |
|     |     | 210 |     |     |     |     | 215 |     |     |      |
| CAG | CAA | GAC | AAG | GAG | CGC | CTG | GCA | GCC | CTG | 1608 |
| Gln | Gln | Asp | Lys | Glu | Arg | Leu | Ala | Ala | Leu |      |
|     |     | 220 |     |     |     |     | 225 |     |     |      |
| GGG | CCT | GAG | GGG | GCC | CAT | GGT | GAC | ACT | ACC | 1638 |
| Gly | Pro | Glu | Gly | Ala | His | Gly | Asp | Thr | Thr |      |
|     |     | 230 |     |     |     |     | 235 |     |     |      |
| TTT | GAG | TAC | CAG | GAC | CTG | TGC | CGC | CAG | CAC | 1668 |
| Phe | Glu | Tyr | Gln | Asp | Leu | Cys | Arg | Gln | His |      |
|     |     | 240 |     |     |     |     | 245 |     |     |      |
| ATG | GCC | ACG | AAG | TCC | TTG | TTC | AAC | CGG | GCA | 1698 |
| Met | Ala | Thr | Lys | Ser | Leu | Phe | Asn | Arg | Ala |      |
|     |     | 250 |     |     |     |     | 255 |     |     |      |
| GAG | GGT | CCA | CCG | GAG | CCT | TCA | CGG | GTG | AGC | 1728 |
| Glu | Gly | Pro | Pro | Glu | Pro | Ser | Arg | Val | Ser |      |

|  |  |  |  |  |  |  |  |  |  |  |
|---|---|---|---|---|---|---|---|---|---|---|
|  |  |  |  | 260 |  |  |  | 265 |  |  |
| AGT | GTG | TCC | TCC | CAG | TTC | AGC | GAC | GCA | GCC | 1758 |
| Ser | Val | Ser | Ser | Gln | Phe | Ser | Asp | Ala | Ala |  |
|  |  | 270 |  |  |  |  | 275 |  |  |  |
| CAG | GCC | AGC | CCC | AGC | TCC | CAC | AGC | AGC | ACC | 1788 |
| Gln | Ala | Ser | Pro | Ser | Ser | His | Ser | Ser | Thr |  |
|  |  | 280 |  |  |  |  | 285 |  |  |  |
| CCG | TCC | TGG | TGC | GAG | GAG | CCG | GCC | CAA | GCC | 1818 |
| Pro | Ser | Trp | Cys | Glu | Glu | Pro | Ala | Gln | Ala |  |
|  |  | 290 |  |  |  |  | 295 |  |  |  |
| AAC | ATG | GAC | ATC | TCC | ACG | GGA | CAC | ATG | ATT | 1848 |
| Asn | Met | Asp | Ile | Ser | Thr | Gly | His | Met | Ile |  |
|  |  | 300 |  |  |  |  | 305 |  |  |  |
| CTG | GCA | TAC | ATG | GAG | GAT | CAC | CTG | CGG | AAC | 1878 |
| Leu | Ala | Tyr | Met | Glu | Asp | His | Leu | Arg | Asn |  |
|  |  | 310 |  |  |  |  | 315 |  |  |  |
| CGG | GAC | CGC | CTT | GCC | AAG | GAG | TGG | CAG | GCC | 1908 |
| Arg | Asp | Arg | Leu | Ala | Lys | Glu | Trp | Gln | Ala |  |
|  |  | 320 |  |  |  |  | 325 |  |  |  |
| CTC | TGT | GCC | TAC | CAA | GCA | GAG | CCA | AAC | ACC | 1938 |
| Leu | Cys | Ala | Tyr | Gln | Ala | Glu | Pro | Asn | Thr |  |
|  |  | 330 |  |  |  |  | 335 |  |  |  |
| TGT | GCC | ACC | GCG | CAG | GGG | GAG | GGC | AAC | ATC | 1968 |
| Cys | Ala | Thr | Ala | Gln | Gly | Glu | Gly | Asn | Ile |  |
|  |  | 340 |  |  |  |  | 345 |  |  |  |
| AAA | AAG | AAC | CGG | CAT | CCT | GAC | TTC | CTG | CCC | 1998 |
| Lys | Lys | Asn | Arg | His | Pro | Asp | Phe | Leu | Pro |  |
|  |  | 350 |  |  |  |  | 355 |  |  |  |
| TAT | GAC | CAT | GCC | CGC | ATA | AAA | CTG | AAG | GTG | 2028 |
| Tyr | Asp | His | Ala | Arg | Ile | Lys | Leu | Lys | Val |  |
|  |  | 360 |  |  |  |  | 365 |  |  |  |
| GAG | AGC | AGC | CCT | TCT | CGG | AGC | GAT | TAC | ATC | 2058 |
| Glu | Ser | Ser | Pro | Ser | Arg | Ser | Asp | Tyr | Ile |  |
|  |  | 370 |  |  |  |  | 375 |  |  |  |
| AAC | GCC | AGC | CCC | ATT | ATT | GAG | CAT | GAC | CCT | 2088 |
| Asn | Ala | Ser | Pro | Ile | Ile | Glu | His | Asp | Pro |  |
|  |  | 380 |  |  |  |  | 385 |  |  |  |
| CGG | ATG | CCA | GCC | TAC | ATA | GCC | ACG | CAG | GGC | 2118 |
| Arg | Met | Pro | Ala | Tyr | Ile | Ala | Thr | Gln | Gly |  |
|  |  | 390 |  |  |  |  | 395 |  |  |  |
| CCG | CTG | TCC | CAT | ACC | ATC | GCA | GAC | TTC | TGG | 2148 |
| Pro | Leu | Ser | His | Thr | Ile | Ala | Asp | Phe | Trp |  |
|  |  | 400 |  |  |  |  | 405 |  |  |  |
| CAG | ATG | GTG | TGG | GAG | AGC | GGC | TGC | ACC | GTC | 2178 |
| Gln | Met | Val | Trp | Glu | Ser | Gly | Cys | Thr | Val |  |
|  |  | 410 |  |  |  |  | 415 |  |  |  |
| ATC | GTC | ATG | CTG | ACC | CCG | CTG | GTG | GAG | GAT | 2208 |
| Ile | Val | Met | Leu | Thr | Pro | Leu | Val | Glu | Asp |  |
|  |  | 420 |  |  |  |  | 425 |  |  |  |
| GGT | GTC | AAG | CAG | TGT | GAC | CGC | TAC | TGG | CCA | 2238 |
| Gly | Val | Lys | Gln | Cys | Asp | Arg | Tyr | Trp | Pro |  |
|  |  | 430 |  |  |  |  | 435 |  |  |  |
| GAT | GAG | GGT | GCC | TCC | CTC | TAC | CAC | GTA | TAT | 2268 |
| Asp | Glu | Gly | Ala | Ser | Leu | Tyr | His | Val | Tyr |  |
|  |  | 440 |  |  |  |  | 445 |  |  |  |
| GAG | GTG | AAC | CTG | GTG | TCG | GAG | CAC | ATC | TGG | 2298 |
| Glu | Val | Asn | Leu | Val | Ser | Glu | His | Ile | Trp |  |
|  |  | 450 |  |  |  |  | 455 |  |  |  |
| TGC | GAG | GAC | TTT | CTG | GTG | CGG | AGC | TTC | TAC | 2328 |
| Cys | Glu | Asp | Phe | Leu | Val | Arg | Ser | Phe | Tyr |  |

```
                    460                              465
CTG  AAG  AAC  GTG  CAG  ACC  CAG  GAG  ACG  CGC                        2358
Leu  Lys  Asn  Val  Gln  Thr  Gln  Glu  Thr  Arg
               470                    475

ACG  CTC  ACG  CAG  TTC  CAC  TTC  CTC  AGC  TGG                        2388
Thr  Leu  Thr  Gln  Phe  His  Phe  Leu  Ser  Trp
               480                    485

CCG  GCA  GAG  GGC  ACA  CCG  GCC  TCC  ACG  CGG                        2418
Pro  Ala  Glu  Gly  Thr  Pro  Ala  Ser  Thr  Arg
               490                    495

CCC  CTG  CTG  GAC  TTC  CGC  AGG  AAG  GTG  AAC                        2448
Pro  Leu  Leu  Asp  Phe  Arg  Arg  Lys  Val  Asn
               500                    505

AAG  TGC  TAC  CGG  GGC  CGC  TCC  TGC  CCC  ATC                        2478
Lys  Cys  Tyr  Arg  Gly  Arg  Ser  Cys  Pro  Ile
               510                    515

ATC  GTG  CAC  TGC  AGT  GAT  GGT  GCG  GGG  AGG                        2508
Ile  Val  His  Cys  Ser  Asp  Gly  Ala  Gly  Arg
               520                    525

ACC  GGC  ACC  TAC  ATC  CTC  ATC  GAC  ATG  GTC                        2538
Thr  Gly  Thr  Tyr  Ile  Leu  Ile  Asp  Met  Val
               530                    535

CTG  AAC  CGC  ATG  GCA  AAA  GGA  GTG  AAG  GAG                        2568
Leu  Asn  Arg  Met  Ala  Lys  Gly  Val  Lys  Glu
               540                    545

ATT  GACATCGCTG  CCACCCTGGA  GCATGTCCGT                                 2601
Ile

GACCAGCGGC  CTGGCCTTGT  CCGCTCTAAG  GACCAGTTTG                           2641

AATTTGCCCT  GACAGCCGTG  GCGGAGGAAG  TGAATGCCAT                           2681

CCTCAAGGCC  CTGCCCCAGT  GAGACCCTGG  GGCCCCTTGG                           2721

CGGGCAGCCC  AGCCTCTGTC  CCTCTTTGCC  TGTGTGAGCA                           2761

TCTCTGTGTA  CCCACTCCTC  ACTGCCCCAC  CAGCCACCTC                           2801

TTGGGCATGC  TCAGCCCTTC  CTAGAAGAGT  CAGGAAGGGA                           2841

AAGCCAGAAG  GGGCACGCCT  GCCCAGCCTC  GCATGCCAGA                           2881

GCCTGGGGCA  TCCCAGAGCC  CAGAGCATCC  CATGGGGGTG                           2921

CTGCAGCCAG  GAGGAGAGGA  AAGGACATGG  GTAGCAATTC                           2961

TACCCAGAGC  CTTCTCCTGC  CTACATTCCC  TGGCCTGGCT                           3001

CTCCTGTAGC  TCTCCTGGGG  TTCTGGGAGT  TCCCTGAACA                           3041

TCTGTGTGTG  TCCCCCTATG  CTCCAGTATG  GAAGAATGGG                           3081

GTGGAGGGTC  GCCACACCCG  GCTCCCCCTG  CTTCTCAGCC                           3121

CCGGGCCTGC  CTCTGACTCA  CACTTGGGCG  CTCTGCCCTC                           3161

CCTGGCCTCA  CGCCCAGCCT  CCTCCCACCA  CCCTCCCACC                           3201

ATGCGCTGCT  CAACCTCTCT  CCTTCTGGCG  CAAGAGAACA                           3241

TTTCTAGAAA  AAACTACTTT  TGTACCAGTG  TGAATAAAGT                           3281

TAGTGTGTTG  TCTGTGCAGC  TGCAAAAAAA                                      3311
```

PANCREATIC ISLET CELL ANTIGENS OBTAINED BY MOLECULAR CLONING

CROSS-REFERENCE TO RELATED APPLICATIONS

This is a continuation of application Ser. No. 07/872,646, filed Jun. 8, 1992, now abandoned, which is a continuation of application Ser. No. 715,181, filed on Jun. 14, 1991, now abandoned, which is a continuation-in-part of application Ser. No. 441,703, filed Dec. 4, 1989 now abandoned, which is a continuation-in-part of application Ser. No. 312,543, filed Feb. 17, 1989 now abandoned.

BACKGROUND OF THE INVENTION

This invention relates to pancreatic islet cell antigens that bind with antibodies found in the sera of patients afflicted with insulin-dependent (Type I) diabetes mellitus (IDDM). More particularly, the invention relates to proteins and peptides that bind with islet cell antibodies (ICA) and that are prepared by recombinant DNA (rDNA) or synthetic methods. The invention also concerns cloned DNA encoding such ICA proteins and peptides. The ICA proteins and peptides of the present invention are useful as immunoassay reagents in the presymptomatic diagnosis of IDDM.

The accumulating evidence of cellular and humoral abnormalities associated with IDDM has led to the hypothesis that the disease is an autoimmune disorder. Serum antibodies directed against the insulin-producing beta cells of the pancreatic islets have been detected by immunofluorescence, [G. F. Bottazzo, A. Florin-Christensen, and D. Doniach: Islet Cell Antibodies in Diabetes Mellitus With Autoimmune Polyendocrine Deficiencies, Lancet ii:1279–1283 (1974), and A. C. MacCuish, J. Jordan, C. J. Campbell, L. J. P. Duncan, and W. J. Irvine: Antibodies to Islet-cell in Insulin-dependent Diabetics With Coexistent Autoimmune Disease, Lancet ii:1529–1533 (1974)]. These autoantibodies are observed in 70–80% of newly diagnosed diabetics (NDD), but only in 0.1–1% of normal control subjects [C. H. Brogren and A. Lernmark: Islet Cell Antibodies in Diabetes. Clin. Endocrinol. Metab. 11:409–430 (1982)], and G. F. Bottazzo, R. Pujol-Borrell, and D. Doniach: Humoral and Cellular Immunity in Diabetes Mellitus. Clin. Immunol. Allergy 1:139–159 (1981)]. ICAs have come to be accepted as one predictive factor for IDDM. A review of current knowledge on ICA is provided by A. Lernmark, Diabetic Medicine 4:285–292 (1987).

The conventional ICA assay consists of exposing pancreas sections to sera, staining with a second antibody bearing either a fluorescent [G. F. Bottazzo et al., supra] or enzyme label [P. G. Colman, M. Tatkus, A. Rabizadeh, C. Cahill, and G. S. Eisenbarth: Assay for Islet Cell Antibodies with Rat Pancreas and Peroxidase Protein A. Diabetes Care 11:367–368 (1988)], and observing under a microscope. Another similar method involves a biotin-avidin sandwich and immunofluorescent detection [T. Kobayashi, T. Sugimoto, T. Itoh, K. Kosaka, T. Tanaka, S. Suwa, K. Sato and K. Tsuju: The Prevalence of Islet Cell Antibodies in Japanese Insulin-dependent and Non-insulin-dependent Diabetic Patients Studied by Indirect Immunofluorescence and by a New Method. Diabetes 35:335–340 (1986)]. These methods are time consuming, laborious, difficult to reproduce, and have limited sensitivity. The development of a more convenient immunoassay for ICA would permit widespread testing for epidemiology and correlation with IDDM, and ultimately prediction of the disease with a screening test.

A major limitation of current ICA tests is the limited knowledge and characterization of the islet cell antigens involved. The ICA's may be of low titer or affinity and approachable only with characterized antigens. ICA antigens that are detected by the immunofluorescence test are of special interest; these antigens may include:

(1) islet cell surface moieties [N. K. MacLaren, S. W. Hugng, and J. Fogh: Antibody to Cultured Human Insulinoma Cells in Insulin-dependent Diabetes. Lancet 1:997–1000 (1975), and A. Lernmark, Z. R. Freedman, C. Hofmann, A. H. Rubenstein, D. F. Steiner, R. L. Jackson, R. J. Winter and H. S. Traisman: Islet-cell-surface Antibodies in Juvenile Diabetes Mellitus. N. Engl. J. Med. 299:375–380 (1978)], (2) insulin [J. P. Palmer, C. M. Asplin, P. Clemons, K. Lyen, O. Tetpati, P. K. Raghu and T. L. Paquette: Insulin Antibodies in Insulin-dependent Diabetics Before Insulin Treatment. Science 222:1337–1339 (1983), and S. Srikanta, A. T. Ricker, D. K. McCulloch, J. S. Soeldner, G. S. Eisenbarth and J. P. Palmer: Autoimmunity to Insulin, Beta Cell Dysfunction, and Development of Insulin-dependent Diabetes Mellitus. Diabetes 35:139–142 (1986)], (3) a 64,000 dalton (64 kd) islet protein of unknown cellular localization [S. Baekkeskov, J. H. Nielsen, B. Marner, T. Bilde, J. Ludvigsson, and A. Lernmark: Autoantibodies in Newly Diagnosed Diabetic Children Immunoprecipitate Human Pancreatic Islet Cell Proteins. Nature 298:167–169 (1982). Recent evidence indicates that the 64 kd protein is glutamic acid decarboxylase (GAD). [S. Baekkeskov, J-H. Aanstoot, S. Christgau, A. Reetz, M. Solimena, M. Cascalho, F. Folli, H. Richter-Olesen and P. De-Camilli: Identification of the 64 k autoantigen in insulin-dependent diabetes as the GABA-synthesizing enzyme glutamic acid decarboxylase. Nature 347:151–156 (1990)], (4) cytoplasmic antigens [G. F. Bottazzo, A. Florin-Christensen, and D. Doniach: Islet Cell Antibodies in Diabetes Mellitus With Autoimmune Polyendocrine Deficiencies. Lancet 2:1279–1283 (1974), A. C. MacCuish, J. Jordan, C. J. Campbell, L. J. P. Duncan, and W. J. Irvine: Antibodies to Islet-Cell in Insulin-Dependent Diabetics With Coexistent Autoimmune Disease. Lancet 2:1529–1533 (1974), R. Lendrum, G. Walker, and D. R. Gambli: Islet-Cell Antibodies in Juvenile Diabetes Mellitus of Recent Onset. Lancet 1:880–883 (1975), and W. J. Irvine, C. J. McCallum, R. S. Gray, G. J. Campbell, L. J. P. Duncan, J. W. Farquhar, H. Vaughan, and P. J. Morris: Pancreatic Islet Cell Antibodies in Diabetes Mellitus Correlated With The Duration and Type of Diabetes, Co-existent Autoimmune Disease, and HLA-type. Diabetes 26:138–147 (1977)], (5) glycoconjugates [R. C. Nayak, M. A. K. Omar, A. Rabizadeh, S. Srikanta, and G. S. Eisenbarth, "Cytoplasmic" Islet Cell Antibodies: Evidence That the Target Antigen is a Sialoglycoconjugate. Diabetes 34:617–619 (1985); P. Vardi, E. E. Dibella, T. J. Pasquarello, and S. Srikanta, Islet Cell Autoantibodies: Pathobiology and Clinical Applications. Diabetes Care 10:645–56 (1987); B. K. Gillard, J. W. Thomas, L. J. Nell and D. M. Marcus, Antibodies Against Ganglioside GT3 in the Sera of Patients with Type I Diabetes Mellitus. Journal of Immunology 142:3826–32 (1989)].

Several reports indicate a high prevalence of anti-64 kd antibody in prediabetic sera as well as is newly diagnosed diabetic sera [S. Baekkeskov, M. Landin, J. K. Kristensen, S. Srikanta, G. Jan Bruining, R. Mandrup-Poulsen, C. de Beaufort, J. S. Soeldner, G. Eisenbarth, F. Lindgren, G. Sundquist, and A. Lernmark: Antibodies to a 64,000 MW Human Islet Cell Antigen Precede the Clinical Onset of Insulin-dependent Diabetes. J. Clin. Invest. 79:926–934 (1987), M. A. Atkinson, N. K. Maclaren, W. J. Riley, D. W. Sharp and L. Holmes: Mr 64,000 Autoantibodies (64 KA) Predict Insulin Dependent Diabetes. American Diabetes Assoc. 48th Annual Meeting (1988) Abstract #391, and M. A. Atkinson, N. K. Maclaren, D. W. Scharp, P. E. Lacy, and W. J. Riley: 64000 Mr autoantibodies as predictors of insulin-dependent diabetes. The Lancet 335:1357–1360 (1990)].

Some other molecular species have been characterized by Western blotting as being "common antigens" recognized by diabetic sera [D. G. Karounos, V. J. Virta, L. J. Nell, and J. W. Thomas: Analysis of Human and RINm5F Islet Cell Antigens. American Diabetes Assoc. Res. Symp. Woods Hole, Mass. October 1987; Abstract #120]. These antigens have molecular weights of 150 kd, 84 kd, 60 kd, 49 kd, and 36 kd. A more recent report from the same laboratory indicates that there is a RIN antigen of Mr 52,000 that reacts with 29% of diabetic sera. [D. G. Karounos and J. W. Thomas: Recognition of Common Islet Antigen by autoantibodies From NOD Mice and Humans With IDDM. Diabetes 39:1085–1090 (1990), D. G. Karounos, L. J. Nell, and J. W. Thomas: Autoantibodies present at onset of type I diabetes recognize multiple islet cell antigens. Autoimmunity 6:79–91(1990), and D. G. Karounos, J. S. wolinsky, B. K. Gillard, and J. W. Thomas: Molecular Mimicry in Type I Diabetes: An Antigenic Determinant on a Rubella Virus Protein is Shared with a 52 kD Beta Cell autoantigen. Diabetes 39:96A (1990)]. The first and third references indicate that the 52,000 antigen is RIN specific, not found in human islets or other tissue.

SUMMARY OF THE INVENTION

The present invention provides a series of cloned nucleic acids that code for one or more proteins or protein fragments which bind selectively with pancreatic islet cell antibodies (ICA). Such cloned nucleic acids are characterized by the cDNA inserts in deposited recombinant bacteriophages ATCC 40550, 40551, 40552, 40553, 40554, 40703, 40704, 40705, 40706, and ICA-512.3.

The present invention, accordingly, also provides ICA proteins and peptide fragments thereof which are encoded by the cloned nucleic acids and are useful in the diagnosis of insulin-dependent (Type I) diabetes mellitus (IDDM). The ability of such proteins and peptides to bind to the antibody combining site on ICAs also confers utility in the binding or blocking of human immunoglobulin, T-cells or B-cells involved in IDDM, including circulating immunoglobulin, T-cells, and B-cells.

The ICA proteins and peptides of the present invention are obtained by such methods as full or partial expression, optionally with subsequent fragmentation, of the present cloned nucleic acids; and peptide or polypeptide synthesis based on the amino acid sequences determined from the present cloned cDNAs or from the full length ICA antigen genes that can be determined or isolated from islet cell nucleic acid libraries with the aid of the present complementary cloned cDNA sequences. Accordingly, such ICA proteins and peptides include the full length ICA proteins present in or on islet cells and which are expressed by the human gene whose mRNA is at least in part complementary with the complete sequence of the present cloned cDNAs.

Also included in the ICA proteins and peptides of the present invention are the proteins expressed by recombinant cloning vehicles comprising the present cDNA inserts and fragments of such proteins obtained by partial expression or by subsequent fragmentation such as with restriction nucleases. The ICA proteins and peptides of the present invention also include peptides obtained by protein synthesis, such as those that are 3 amino acids in length or longer, which represent ICA epitopes or analogues or derivatives thereof.

The present invention offers a number of significant advantages. The molecular cloning of ICA antigens affords the preparation of large and reproducible amounts of material for use in research, diagnosis, and treatment of IDDM, as well as the opportunity to study the biological mechanisms involved in islet cell destruction and the appearance of ICA. The availability of large quantities of pure antigen enables the development of highly sensitive and specific immunoassays which can be used to screen the general population for presymptomatic IDDM or a predisposition to develop IDDM.

BRIEF DESCRIPTION OF THE DRAWINGS AND SEQUENCE LISTING

FIGS. 1A–5B, 8A, 8B, 9A and 9B are reactivity profiles of ATCC-deposited ICA clones prepared in accordance with the present invention with diabetic and normal sera under conditions described in the Examples.

FIGS. 7 and 10 are summaries of the sera profiles of ICA clones showing reactivity values assigned by visual interpretation of the profiles in FIGS. 1A–5B, respectively.

Figure 1B:
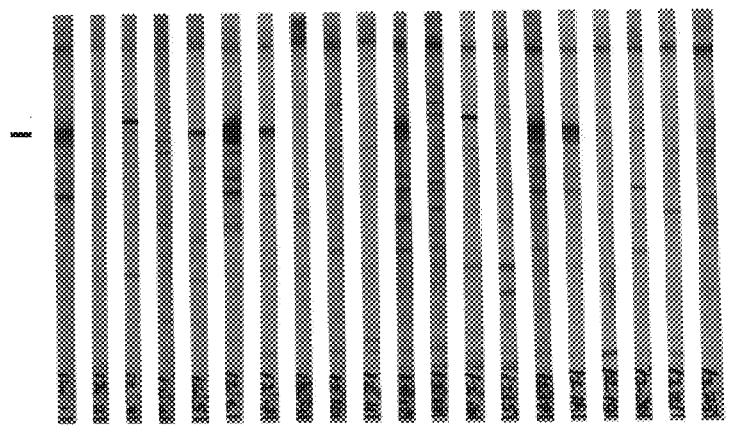
Figure 1A:
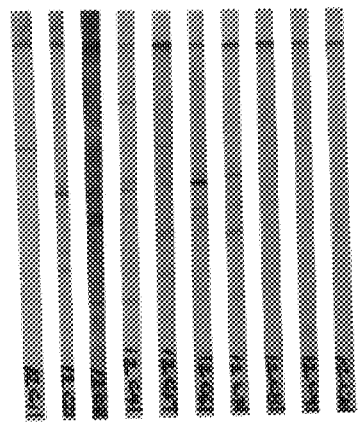
Figure 2A:
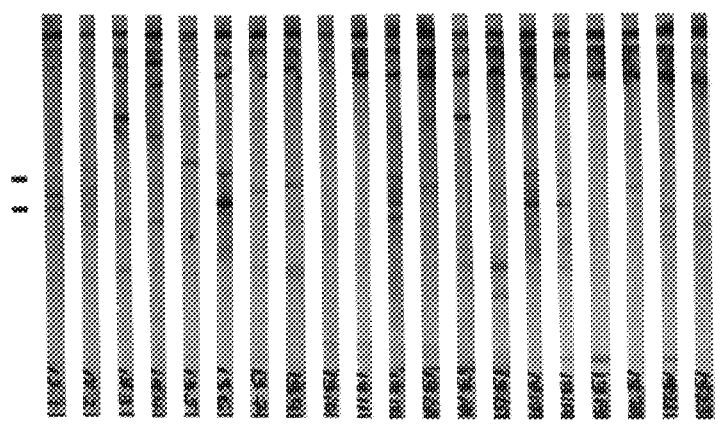
Figure 2B:
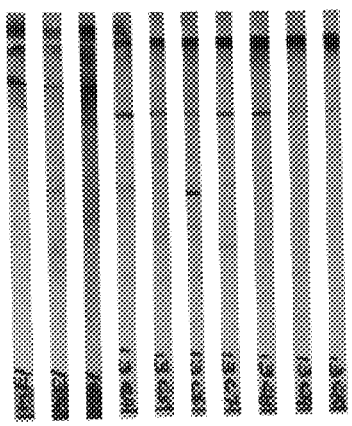
Figure 3A:
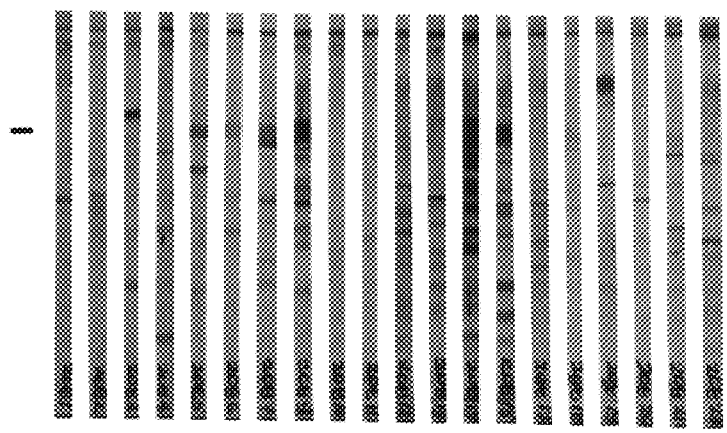
Figure 3B:
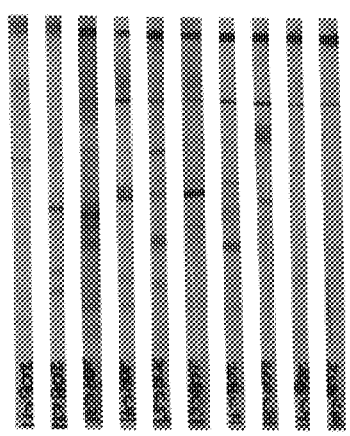
Figure 5A:
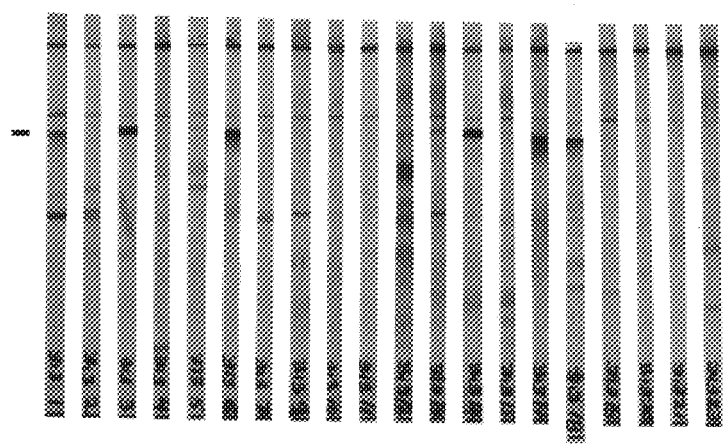
Figure 5B:
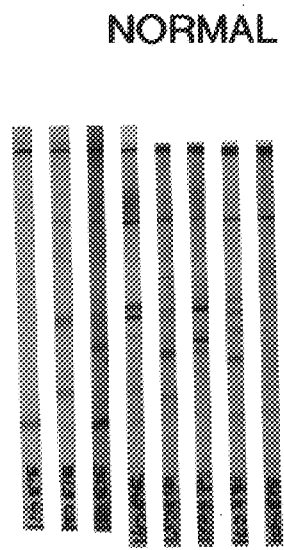

The sequence listing provides the DNA and inferred protein sequences for particular ICA clones as following:

| SEQ ID NO. | ICA CLONE |
| --- | --- |
| 1 | 12 |
| 2 | 13 |
| 3 | 208 |
| 4 | 302 |
| 5 | 313 |
| 6 | 12.3 |
| 7 | 525 |
| 8 | 505 |
| 9 | 512 |
| 10 | 512.3 |

DESCRIPTION OF THE PREFERRED EMBODIMENTS

As used herein, the term "ICA antigens" shall be understood to refer to the proteins and peptides provided by the present invention even though it is recognized that in some cases peptide forms will not be "antigens" in the strict sense, i.e., they will be haptenic since they will require attachment to a conventional macromolecular carrier in order to stimulate the production of antibodies in a host animal.

Furthermore, the "cloned nucleic acids", "cloned ICA antigen sequences", "cDNA inserts", and like terms shall refer to the inserts in deposited recombinant phages ATCC 40550, 40551, 40552, 40553, 40554, 40703, 40704, 40705, 40706, and ICA-512.3, and also to other nucleic acid sequences of full length genes, or fragments of such sequences, comprising such deposited sequences. It will be recognized that one or more full length ICA antigens are characterized by homology with the above deposited cDNA inserts, however, it is possible that two or more of such cDNA inserts correspond to a single ICA antigen. For example, the insert in ATCC 40703 appears to encompass the inserts for both ATCC 40550 and ATCC 40554, and thus these three inserts may all correspond to different and/or overlapping portions of a single ICA antigen. Moreover, ATCC 40706 is comprised in ICA-512 .3.

Preparation of Cloned ICA Antigen Sequences

In general, the cloned ICA antigen sequences of the present invention are obtained by expressing human genes in a suitable recombinant cloning vehicle, e.g., bacteriophage, and probing the resulting gene library with IDDM serum to select antigens that are recognized by ICA antibodies. Recombinant antigens are then screened with a panel of diabetic and normal sera to determine the disease specificity of the identified clones.

The particular deposited clones were more particularly obtained by the following method (further details can be found in the Examples below). A human cDNA library was generated by extracting RNA from purified human islets. This RNA was fractionated by chromatography to separate poly-A mRNA from other RNA such as ribosomal RNA and fragments of degraded RNA. The separated mRNA was reverse transcribed with a commercially available cDNA kit (Bethesda Research Laboratories), ligated to Eco RI DNA linkers, and ligated into lambda gt-11 arms for in vitro packaging. The ligated lambda was packaged using a commercial kit (Stratagene) and then amplified on a bacterial lawn in a plate format.

The phage library was screened with antibodies from autoimmune patients with Type I diabetes. Agarose plates were spread with bacteria infected with the phage, and recombinant protein expression was induced chemically. The protein was deposited onto filters which were then probed with serum. Plaques that appeared to be positive were isolated from the agarose plates and purified through two rounds of isolation. Subsequent to cloning, the gt-11 phage was infected into a bacterial host for large scale expression. Specificity of the proteins expressed by the cloned cDNA was evaluated by Western blotting of bacterial extracts containing the cloned human protein. Preparative polyacrylamide gels were run and electroblotted onto membranes, the membranes were cut into strips, and then reacted with a series of normal and diabetic sera. The clones that generated proteins that reacted exclusively or predominantly with diabetic sera were selected.

Recombinant Cloning Vehicles and Subcloning

As is conventionally known in the art, the cDNA transcripts of the present invention, such as library cDNA or cDNA inserts excised from a cloning vehicle, can be incorporated into a variety of recombinant cloning vehicles for amplification of sequences of interest and for expression of ICA antigens of interest. A recombinant cloning vehicle will be understood to be a biochemical molecule or structure, e.g., DNA, that allows insertion of polynucleotide sequences and replication of the inserted polynucleotide sequences when the vehicle is appropriately incorporated into a host cell. An expression vehicle additionally includes the property of expressing the protein encoded by the inserted polynucleotide. In an expression vector, the inserted ICA antigen sequence is operably linked to a suitable control sequence capable of effecting the expression of ICA antigen in a suitable host. The control sequence involved will vary according to the host and transformation method selected. These matters are within the ordinary skill of the art.

Suitable recombinant cloning vehicles include plasmids, viruses and bacteriophage, and integratable fragments of DNA (i.e., fragments integratable into the host genome by recombination). Expression vehicles are particularly preferred and are exemplified, without limitation, by bacterial pEMBL, pMMB, pUK, pATH, and pGEX, yeast pAAH5, pYE4, and pAB112, mammalian pRSV, vaccinia derived vectors, baculovirus derived vectors, papilloma derived vectors, retroviral vectors, and shuttle vectors such as pCDM8. For a review, see D. M. Glover, DNA Cloning: A Practical Approach (1985) IRL Press Ltd. Suitable host cells include procaryotes, yeast, and higher eucaryotic cells including mammalian cells.

Subcloning of cDNA inserts can involve excising the insert for ligation into a different cloning vehicle. The insert can be excised using the restriction enzyme corresponding to the linkers used in the original insertion or using restriction enzymes selected from a restriction map of the insert. The excised cDNA can be inserted into another suitable vector for sequencing, amplification, or expression as desired. Should the terminal restriction sites in the original cloning vehicle have been destroyed, other enzymes can be used to recover the insert and resulting flanking regions from the cloning vehicle deleted by conventional means.

Another method of preparing DNA fragments for insertion into a cloning vehicle is the use of polymerase chain reaction (PCR) amplification. This procedure can be used on ligation reaction products to amplify the amount of DNA and introduce desired restriction sites for subcloning. PCR can also be used to replicate a fragment with desired restriction sites for transfer from one vehicle into another vehicle.

Full-Length Gene Cloning

Fragments of the cDNA inserts of the present invention can be used to isolate full-length cDNA or genomic DNA clones from appropriate libraries by standard methods. The target library is spread on plates, allowed to grow, transferred to filters, and reacted with DNA probes. Such DNA probes are generated from restriction fragments of the cDNA inserts by such methods as end labeling, nick translation, random primed transcription, or photochemical means. Oligonucleotides can be synthesized, labeled, and used as hybridization probes. RNA probes can also be generated from subcloned cDNA by transcription from appropriate templates.

Recombinant cloning vehicles, e.g., phage or plasmids, that appear to react with the partial cDNA clones are re-screened and then restriction mapped. Promising clones are then sequenced to confirm the hybridization of the original probes and to obtain extended sequence information on the larger fragment. If full-length clones are not obtained in this procedure, the complete sequence of the nucleic acid coding for the human gene can be pieced together from overlapping sequences of cloned fragments.

An alternative method for obtaining longer fragments, and possibly full-length clones, uses antibodies raised against ICA antigens expressed by partial clones. After identifying an antigen of interest, it can be used as an immunogen to raise monoclonal or polyclonal antibodies of high titer and affinity. Such antibodies will enable the detection of longer cDNA clones and cDNA clones present in lower amounts in the library.

Antigen and Peptide Synthesis

ICA antigens, as defined herein, can be prepared in a number of different ways from the clones and sequence information provided by the present invention. One can simply express the proteins from ICA antigen clones obtained according to the present invention, particularly from the deposited clones. Such expressed proteins, or fragments or digestion products thereof, can be used as antigens for binding to islet cell antibodies. However, direct use of bacterial expression extracts may not be possible in some cases since human sera normally react nonspecifically with *E. coli* proteins. In such cases, the expressed ICA antigens can be isolated by conventional techniques such as electrophoretic separation followed by immobilization on membranes (Western blotting), or by column chromatography or affinity purification (e.g., anti-beta-galactosidase affinity resin chromatography or other conventional biochemical means, e.g., salt or temperature precipitation).

Alternatively, peptide fragments can be synthesized by well-known methods from the amino acid sequences deduced from experimentally determined DNA sequences of ICA antigen clones. Overlapping peptides can be synthesized and tested for reactivity with ICA sera. As reactive peptides are found, smaller peptides can be prepared in order to map the smallest reacting unit, i.e., the epitope.

Methods

A principal use of the ICA antigens provided by the present invention is in the diagnosis and prediction of IDDM. In such a method, a blood sample, normally a serum sample, is reacted with a selected one or series of ICA antigens and immunoreactivity determined by any conventional technique. It is further contemplated that the immunoreactivity profile with different ICA antigens can provide diagnostically significant information concerning the nature of the disease, e.g., subtypes, the state of the disease, the proximity to onset of the disease, the efficacy of therapy, e.g., immune therapy, and the like.

A further use of the present ICA antigens is in the identification, marking, or specific destruction of autoreactive B-cells. If autoantibodies have a deleterious effect in IDDM, it is contemplated that anti-B-cell therapy can slow or stem the progress of the disease from prediabetes to clinical IDDM.

Another use of the present ICA antigens is in the identification of islet-reactive T-cell populations. ICA antigens can serve as stimulating antigens for T-cell culture, permitting significantly improved T-cell cloning, identification, and growth. It is contemplated that ICA T-cell detection can be significant in the diagnosis of the pre-diabetic state, and that monitoring the level of autoreactive T-cells can give an indication of the progress of the disease and the utility of immune modulating therapies. Further, the generation of ICA T-cell cultures can provide an in vitro model for designing diabetic therapies. Finally, it is contemplated that T-cell immunization can halt or retard autoimmunity by generating a humoral response against self-destructive elements.

The ability of ICA antigens to bind to human ICA immunoglobulin and T-cells can be used to block the binding of ICA to islet cells and islet cell components in vivo, and therefore are contemplated to provide a direct therapeutic effect.

The present invention will now be illustrated, but is not intended to be limited, by the following examples.

EXAMPLES 1. cDNA Library

Islets of Langerhans were purified by Dr.'s Paul Lacy and David Scharp at Washington Univ., St. Louis, Mo., U.S.A., following a published procedure. [C. Ricordi, P. E. Lacy, E. H. Finke, B. J. Olack, and D. W. Scharp: An Automated Method for Isolation of Human Pancreatic Islets. Diabetes 37:413–420 (1988)]. Briefly, human pancreas was perfused with collagenase and then ground up. Ficoll gradient centrifugation was used to isolate the islets, which were then cultured for 1 week at room temperature. The islets were frozen and shipped.

Upon receipt, the islets were thawed, pooled, and washed. RNA was extracted using guanidinium thiocyanate and selectively precipitated with lithium chloride [G. Cathala, J. F. Savouret, B. Mendez, B. L. West, M. Karin, J. A. Martial, and J. D. Baxter: A Method for Isolation of Intact, Transtationally Active Ribonucleic Acid. DNA 2:329–335 (1983)]. About 770 $\mu$g of total RNA was obtained from each ml of centrifuged islets. Messenger RNA was purified using Pharmacia Oligo(dT)-cellulose Type 7 (Pharmacia Fine Chemicals, Piscataway, N.J., U.S.A.), following the procedure of Maniatis et al, [T. Maniatis, E. F. Fritsel, and J. Sambrook: Molecular Cloning, A Laboratory Manual (1982) Cold Spring Harbor Laboratory p. 197–198]. About 30 $\mu$g RNA was obtained after chromatography. In vitro translation using a BRL kit #8110 (Bethesda Research Laboratory, Gaithersburg, Md., U.S.A.), and $^{35}$S-methionine showed a broad range of molecular weight proteins being produced.

A BRL #8267SA kit was used for cDNA synthesis. Ten (10) $\mu$g of poly-A$^+$ RNA was used in the reaction. The ends were polished with $T_4$-DNA polymerase (Pharmacia), and the cDNA was methylated with Eco RI methylase (New England Biolabs, Beverly, Mass., U.S.A.) and S-adenosyl methionine and ligated to Eco RI linkers. The cDNA was digested with Eco RI and run on a Biogel A15M column (BioRad Laboratories, Rockville Center, N.Y., U.S.A.) to separate the linkers and fragments.

The cDNA was ligated into lambda gt-11 arms and packaged with a Stratagene Gigapack Plus kit (Stratagene Cloning Systems, LaJolla, Calif., U.S.A.). A library of approximately 8.5×10$^5$ insert-containing clones was obtained (measured with 5-bromo-4-chloro-3-indolyl-β-D-galactopyranoside), and amplified on *E. coli* Y1090 (Stratagene).

2. Sera

Sera from newly diagnosed diabetics were obtained from Dr. William Riley at the University of Florida, Gainesville, Fla., U.S.A., and Dr. Alan Drash at the Children's Hospital of Pittsburgh, Pittsburgh, Pa., U.S.A.. Normal (non-diabetic) sera were collected from individuals in the laboratory. Sera from non-diabetic children were obtained from Dr. Jocelyn Hicks at the Children's National Medical Center in Washington, D.C. Sera were multiply adsorbed with filters that were prepared either by (a) lysing lambda-infected *E. coli* with chloroform and soaking nitrocellulose filters in this lysate, or (b) preparing filters by overlaying filters soaked with isopropyl-β-thio-galactopyranoside (IPTG) on lambda-infected *E. coli* in a plate format, essentially in the same manner as screening the library. Sera were diluted 1/20-1/200 in blotto solution (5% Carnation non-fat dry milk, 10 mM Tris pH 8.0, 150 mM NaCl, 0.05% Tween-20, and 0.05% sodium azide) after crude fractionation as noted below. Sera were used for ELISA experiments without preadsorption.

3. Screening

The screening procedure is based on standard protocols (T. V. Huynh, R. A. Young and R. W. Davis: Constructing and Screening cDNA Libraries in Fgt 10 and Gft 11 in DNA Cloning. D. M. Glover ed. (1985) IRL Press p. 490–78). Filters were prepared by plating about 50,000 plaque forming units (pfu) of the library onto each of ten 150 mm agarose plates. After growth at 42° C. for about 3 hours, filters (Nitrocellulose from Schleicher and Schuell, Keene, N.H., U.S.A.) containing IPTG were laid onto the plates and growth was continued at 37° C. for either 3–4 hours or overnight. Filters were blocked with a blotto solution and stored at 4° C.

Initially, all antibody reactions with filters were performed at room temperature for 3 hours. In later experiments, sera incubations were done overnight at 4° C. in blotto solution without Tween-20, while secondary antibody reactions were done at room temperature for 1.5 hours. All incubations and washing were done on platform shakers with gentle rotation.

The library was screened with human antibody probes several times. In the first instance, antibody was purified from diabetic sera by HPLC. In the second and third, sera were precipitated with 50% ammonium sulfate and dialyzed. For the first and third screenings, a mixture of two sera were used for all rounds of purification. For the second screening, a mixture of 20 diabetic sera was used for the primary purifications. In a further screening, 22 sera were pooled, precipitated with ammonium sulfate and dialyzed, and the final working dilution of each serum was 1/500 in blotto without Tween 20.

After incubation in the diabetic sera, filters were washed 5–10 minutes each in Tris-buffered saline (TBS), TBS with 0.05% Tween-20, and then in TBS. Human antibody bound to the filters was detected by reaction with rabbit anti-human IgG conjugated to alkaline phosphatase (1/500 in blotto, Dakopatts antibody D-336—DAKO Corp., Santa Barbara, Calif., U.S.A.). Filters were washed in TBS/Tween-20, TBS, TBS, and then detection buffer (0.1M Tris-HCl, pH 9.5, 0.1M NaCl, 0.05M $MgCl_2$, recommended by BRL for use in their DNA detection kit No. 8239SA). Chromogenic substrates (nitro-blue tetrazolium and 5-bromo-4-chloro-3-indolyl phosphate) were added and the reaction was protected from light. After color development, the filters were washed in water, then in 10 mM Tris (pH 8.0), 1 mM EDTA (TE) and dried. Best observation of the plaques could be made when the filters were still matte wet.

Positive plaques were located on the original plates by alignment with the filters. For primary screens, a plug containing a positive plaque was removed using the butt end of a sterile Pasteur pipet. For subsequent screenings where individual plaques could be distinguished, the tip of the pipet was used. Plaques were eluted into plaque storage buffer (Maniatis et al., supra) and eluted for at least several hours.

The above screening methods produced the specific deposited ICA clones described herein with the exception of ICA-12.3 and ICA-512.3 which were isolated as follows.

Approximately $10^6$ plaque forming units of the phage library were screened by DNA hybridization for the presence of sequences homologous with the ICA-12 cDNA. The phage plaques distributed over 20 agar plates were replicated onto nylon filters, and the phage DNA was denatured and immobilized for hybridization, by the conventional procedure of Benton and Davis (1977) Science 196:180. The hybridization probe was an agarose gel-purified sample of the cloned ICA-12 cDNA separated from its plasmid vector by Eco RI digestion. The cDNA segment was tagged with $^{32}P$ by the random primer labeling method (Feinberg and Vogelstein (1984) Anal. Biochem. 137:266). Hybridization of the probe to nylon filters was done according to Berent et al. (1985) BioTech. 3:208. Phage plaques identified as containing DNA homologous with the ICA-12 probe were picked from the master plates, and the phage were replicated for a second round of hybridization screening. Individual plaques remaining positive for ICA-12 sequences were then characterized as to properties of cDNA inserts. The clone ICA-12.3 was found by DNA sequence analysis to contain the entire protein coding sequence of the mRNA partially represented in ICA-12.

Monoclonal antibodies (mAb) were raised using GST-ICA-512 (see below) as immunogen. A mixture of culture supernatants from three mAb clones were pooled and used to screen the human islet lambda-gt11 expression library. The screening method was as described above, except that an alkaline phosphatase conjugated rabbit anti-mouse Ig (DAKO) was used as a second antibody. Clone ICA-512.2 was obtained and determined to have 670 bases more than ICA-512 on the 5' end.

Since it appeared that ICA-512.2 did not contain the initiation site for the full length protein, a DNA probe was made by labelling a 230 base Pst I restriction fragment that was derived from the 5' section of ICA-512.2, (bases 201–431, corresponding to bases 1216–1446 of ICA-512.3, shown in SEQ ID NO 10). This fragment was used to screen the library, and clone ICA-512.3 was identified. SEQ ID NO 10 shows the DNA and inferred protein sequence of this clone.

4. Expression

The proteins expressed by individual clones were analyzed by expressing the clones in E. coli hosts. Initial expressions with clones identified as ICA-12 and ICA-13 were done with lysogens generated with the clones by standard means (Huynh, et al.). Subsequent expressions were done by infective expression into E. coli CAG-456 [M. Snyder, S. Elledge, D. Sweetser, R. A. Young, and R. W. Davis: Fgt-11: Gene Isolation with Antibody Probes and Other Applications, Meth. Enzymology 154:107–128 (1987) ]. Cells were harvested and lysed by resuspension in Laemmli sample buffer [U. K. Laemmli, Nature 227:680 (1970)]. Better electrophoresis results were obtained when samples were sonicated to reduce the size of the DNA and reduce viscosity.

Protein gel electrophoresis and semi-dry electrotransfer onto either nitrocellulose (Schleicher and Shuell) or Immobilon (Millipore Company, Bedford, Mass., U.S.A.) were performed. Gels were stained with Coomassie Blue and filters were detected by immunoreaction with the same sera used to screen the library as detailed above.

5. Clone Analysis

In order to assess the usefulness of the individual clones for diagnosis of IDDM, each clone was tested for reactivity with a panel of diabetic and normal sera. This was done by reacting each serum with a Western blot strip from each clone. Preparative gel electrophoresis was followed by semi-dry electrotransfer of the proteins to filters. Identical 3 mm strips were cut from the filters and exposed to the various sera. Localization of antigen bands was done by reference to analytical Western blots and strips reacted with anti-beta-galactosidase antibody (1/2000 monoclonal antibody from Promega, Madison, Wis., U.S.A.). Antibody incubation and detection with secondary antibody were described above.

The reactivity profiles of the clones identified as ICA-12, ICA-13, ICA-208, ICA-302, ICA-313, ICA-505, and ICA-525 are shown in FIGS. 1–5, 8 and 9 of the drawings.

Figure 6A:
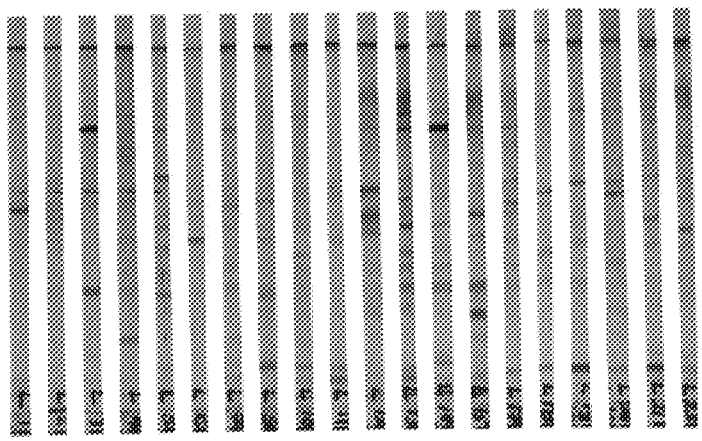
FIGS. 6A and 6B is a control profile using the cloning phage with no recombinant insert.
Figure 6B:
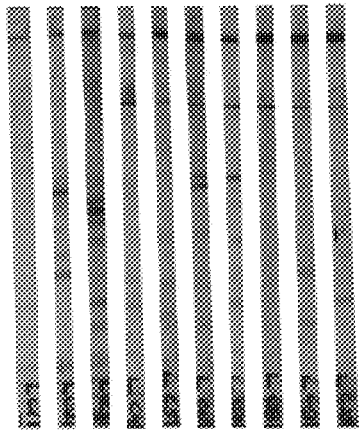
Figure 8A:
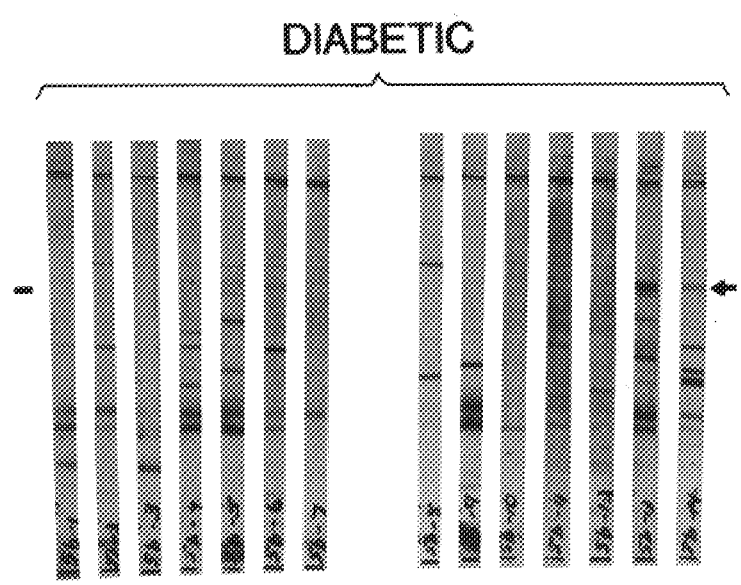
Figure 8B:
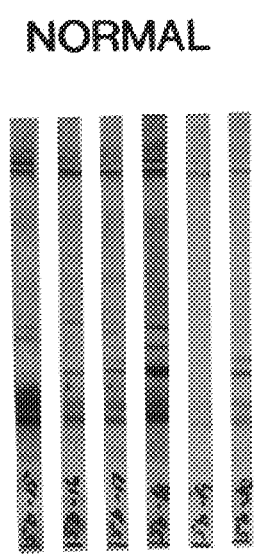
Figure 9A:
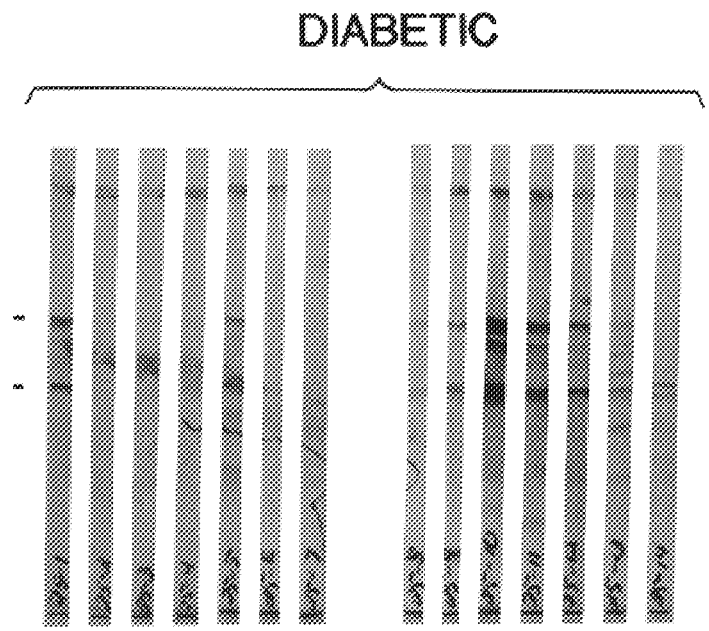
Figure 9B:
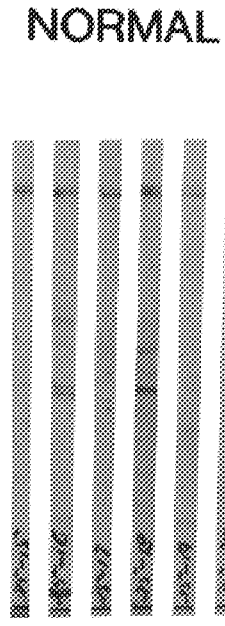

Identical filter strips were cut from preparative electrotransfer and reacted with diabetic and normal sera (for ICA-12, 13, 208, 302, and 313, the strips were reacted with 20 diabetic and 10 normal sera; while 14 diabetic and 6 normal sera were used for ICA-505 and 525). A control profile using the vector (lambda gt-11) having no DNA insert is shown in FIGS. 6A and 6B.

The filter strips were also rated according to intensity, 1=weak reactivity, 2, 3 and 4=very strong reactivity. Summaries of the reactivity ratings are given in FIGS. 7 and 10 of the drawings. In FIG. 7, sera 21–30 bearing the prefix "c" are the normal control sera, while the diabetic sera are presented with their source identification number. In FIG. 10, sera 15–20 bearing the "MRC" prefix are normal control sera, while again the diabetic sera are presented with their source identification numbers. In both Figures, the numbers shown under the clone headings represent the strength of immunoreactivity assigned by visual interpretation.

Some clones identified in the first screening were found to be unreactive in the Western blot format. To test the serum reactivity of these clones, the lambda gt-11 phage were expressed in *E. coli* CAG456 as above and the antigen was extracted by treating the bacteria with 4 mg/ml lysozyme (Sigma, St. Louis, Mo., U.S.A.) in 25 mM Tris, pH 8, 10 mM EDTA, 50 mM glucose and 2 mM phenylmethyl sulfonyl chloride (PMSF) for 5 minutes at room temperature. Cells were pelleted at 4° C. and resuspended in ice cold buffer (500 mM sodium chloride, 1% NP-40, 50 mM Tris, pH 8, 1 mg/ml aprotinin (Sigma), 2 mM PMSF, 2 μg/ml chymostatin (Sigma), 2 μg/ml Antipain (Sigma) and 2 μg/ml pepstatin. Extraction of antigen proceeded for 30 minutes on ice, during which time the solution was sonicated. Samples were spun in an Eppendorf microfuge for 5 minutes at 4° C. and supernatants were used for immunoprecipitation.

Figure 11A:
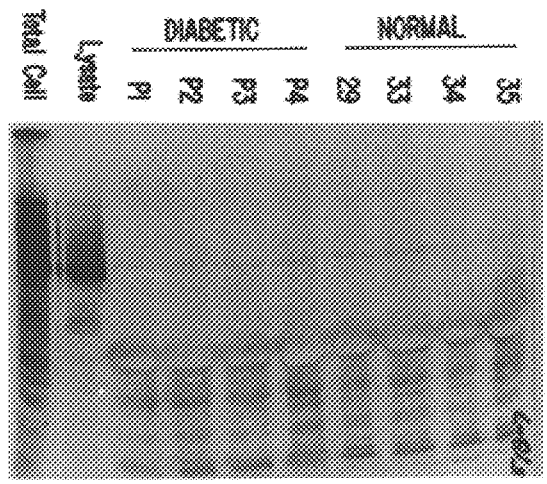
FIGS. 11A–11D shows the results of immunoprecipitation of one of the ICA clones with diabetic and normal sera.
Figure 11B:
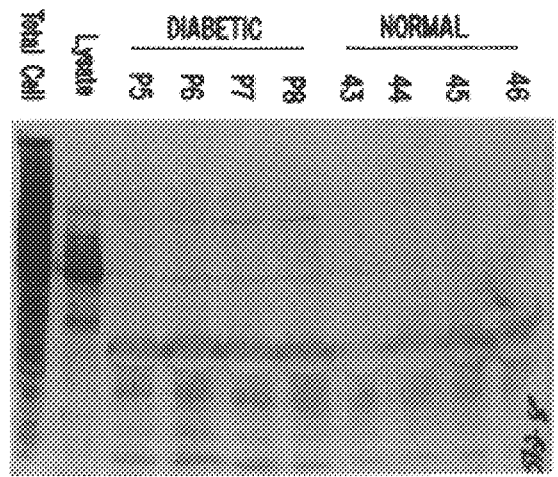
Figure 11C:
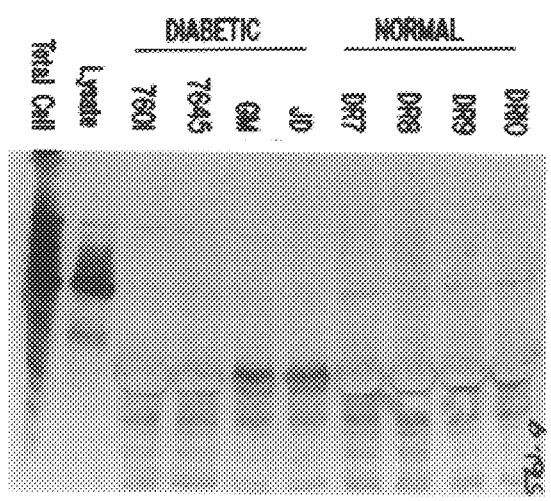
Figure 11D:
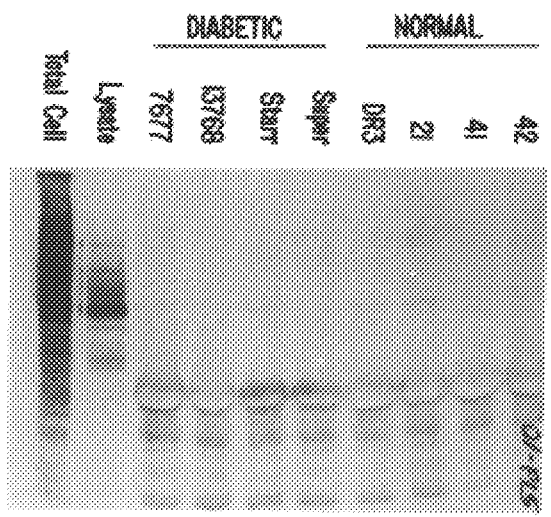

Immune reactions consisted of: 15 μl wash buffer (50 mM Tris, 150 mM sodium chloride, 1% NP-40, 5 mM EDTA, 2 mM PMSF, 2.5 μl human serum, and 10 μl extract. Reactions were left overnight. Antigen-antibody complexes were recovered with 20 μl of a 50% slurry of Protein-A Sepharose CL-4B (Pharmacia) for 1 hour on ice. The resin was washed six times with 500 μl of wash buffer and once with water. Sample buffer for PAGE was added and the samples were boiled for 5 minutes, centrifuged for 5 minutes and run on 8% gels. Electroblotting was performed and the blots reacted with anti-beta-galactosidase antibody (1/1000 dilution of Sigma #G4644 in blotto solution) followed by anti-mouse Ig coupled to alkaline phosphatase (DAKO #D314) and development in dyes. The results are shown in FIGS. 11A and 11B for an extract of ICA-512. Arrows indicate the position of the recombinant antigen.

DNA insert size for the various clones was determined by growing them either in a plate lysate or liquid lysate format (Maniatis, et al., supra). Lambda DNA was extracted, and cut with Eco RI, and analyzed for size by agarose gel electrophoresis.

The above identified clones which reacted predominantly with diabetic sera have been deposited with the American Type Culture Collection, Rockville, Md., U.S.A.. The SEQ ID NOs, deposit numbers, deposit dates, and determined insert sizes are shown in Table 1 below. All restrictions upon public access to these deposits will be irrevocably removed upon the grant of a patent and each deposit will be replaced if viable samples cannot be dispensed by the depository.

TABLE 1

| SEQ ID NO | Clone # | ATCC # | Deposit Date | Insert size (kb) |
|---|---|---|---|---|
| 1 | ICA-12 | 40550 | Feb. 8, 1989 | 1.400 |
| 2 | ICA-13 | 40553 | Feb. 8, 1989 | 5.043 |
| 3 | ICA-208 | 40554 | Feb. 8, 1989 | 0.575 |
| 4 | ICA-302 | 40551 | Feb. 8. 1989 | 0.794 |
| 5 | ICA-313 | 40552 | Feb. 8, 1989 | 2.391 |
| 6 | ICA-12.3 | 40703 | Nov. 14, 1989 | 3.243 |
| 7 | ICA-525 | 40704 | Nov. 14, 1989 | 3.4 |
| 8 | ICA-505 | 40705 | Nov. 14, 1989 | 0.346 |
| 9 | ICA-512 | 40706 | Nov. 14, 1989 | 1.8 |
| 10 | ICA-512.3 | 75030 | June 13, 1991 | 3.3 |

DNA inserts were transferred to a Stratagene Bluescript vector. Sequencing was done by standard techniques using the T7 Sequencing kit (Pharmacia) in conjunction with the Stratagene Exo III/Mung bean nuclease kit for generating overlapping nested deletion series of plasmids.

The sequence is considered to be complete for ICA-12, 302, 313, 208, 505, 12.3, 512, and 512.3, while only partial sequencing is available for ICA-13 and 525. The DNA sequences are those experimentally derived as described above. All three possible reading frames in both orientations were examined for protein coding capability, i.e., long open read frames. The most likely protein sequence for each clone is presented in capital letters below the DNA sequence (except for ICA-505 for which the available information does not permit assignment of the reading frame encoding the protein antigen).

ICA-512 was transferred to a modified version of plasmid pGEX (Pharmacia) for protein expression and purification. This modified plasmid, pGEXc, was adapted for expression of lambda-gt11 products by inserting 2 additional bases between the Bam Hl and EcoRI restriction sites.

A pGEXc clone that was determined to bear the ICA-512 insert in the correct orientation by restriction analysis and DNA sequenceing was expressed following the protocol suggested by the manufacturer (Pharmacia) except that growth after induction with IPTG was at 25° C. Cell lysis, purification of the GST-ICA-512 fusion protein on a glutathione-Sepharose 4B column, cleavage of the fusion protein with thrombin (Sigma T-7009) and purification of the ICA-512 cleaved product with glutathione-Sepharose 4B were performed as described [D. B. Smith and K. S. Johnson: Single-step purification of polypeptides expressed in *Escherichia coli* as fusions with glutathione S-transferase. Gene 67:31–40 (1988)].

ICA-512 was adapted to an ELISA format to provide quantitative information about a large number of samples. Both the GST-ICA-512 and the cleaved ICA-512 were evaluated, and shown to give similar results with a panel of normal and diabetic sera.

Figure 12:
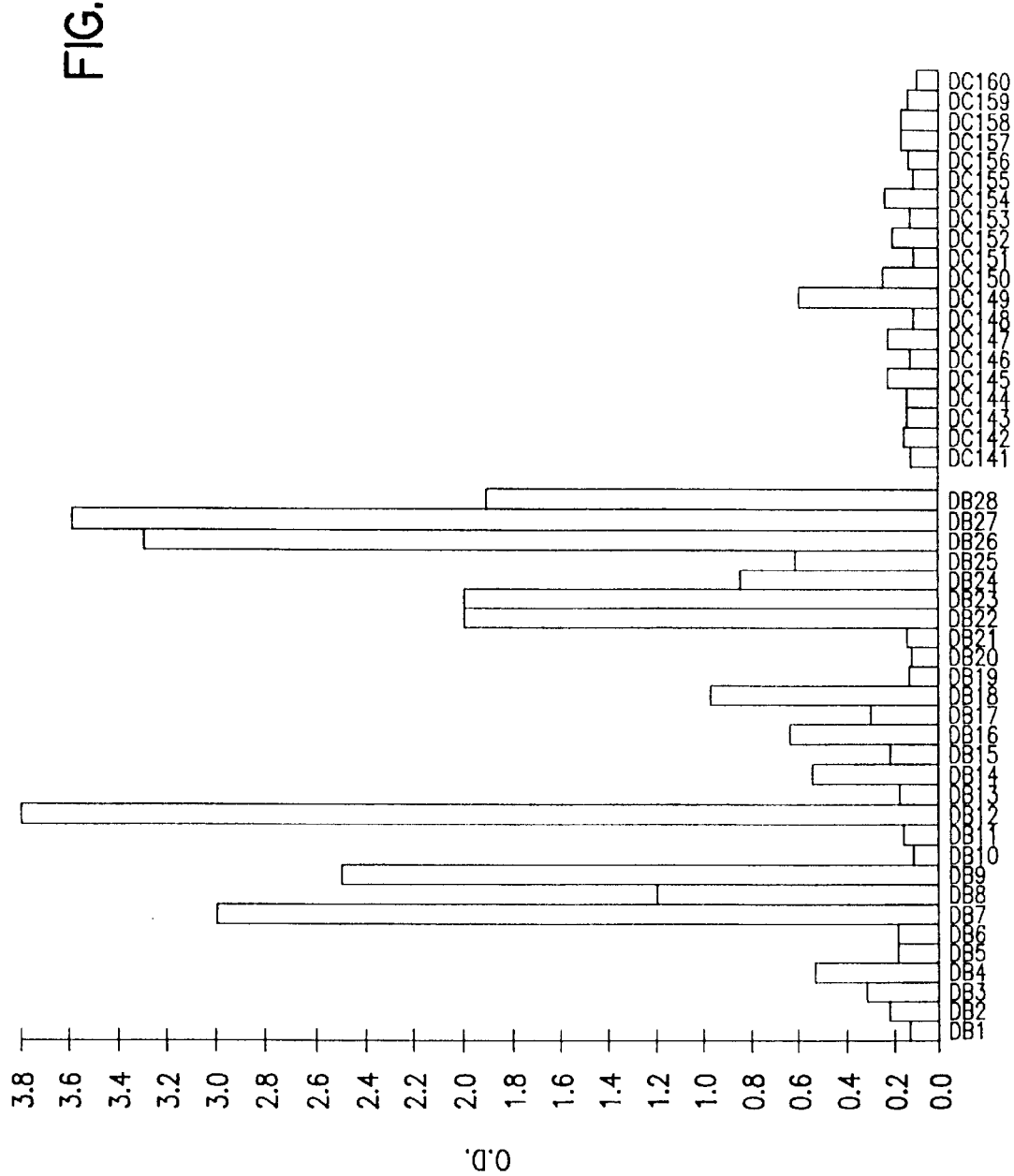
FIGS. 12, 13A and 13B show ELISA profiles illustrating the specificity of reactivity of particular ICA clones (ICA-512 and ICA-12) with diabetic sera.

FIG. 12 shows the reactivity of ICA-512 with such a panel. The "DB" sera on the left are newly diagnosed diabetics, and the "DC" sera on the right are normal sera. In this experiment, 30 ng of cleaved and purified ICA-512 was deposited in each well of an Immulon-2 microtiter plate (Dynatech, Chantilly, Va.) in TBS buffer and allowed to stand overnight. Other coating buffers have been tested and shown to be equivalent. All incubations and reactions were done at room temperature with orbital shaking. Unbound antigen was shaken out. The plate was blocked with a blotto solution containing Tween-20 for 1 hour, and then reacted with 1.5 μl of human serum diluted in 50 μl blotto/Tween. Incubation was for 1 hour. After washing 5 times with PBS/Tween, the wells were incubated with 100 μl of a 1/000 dilution of alkaline phosphatase (AP) conjugated anti-human IgG antibody (Sigma A-0287) for 1 hour. After washing 5 times in PBS/Tween and once for 15 minutes with TBS/Tween, the plate was developed with nitrophenylphosphate (1 Sigma tablet #104–105 in 10 ml of 1M diethanolamine, 0.5 mM MgCl$_2$, pH 9.8) for 1–2 hours. Optical density was read at 405 nm.

Figure 13A:
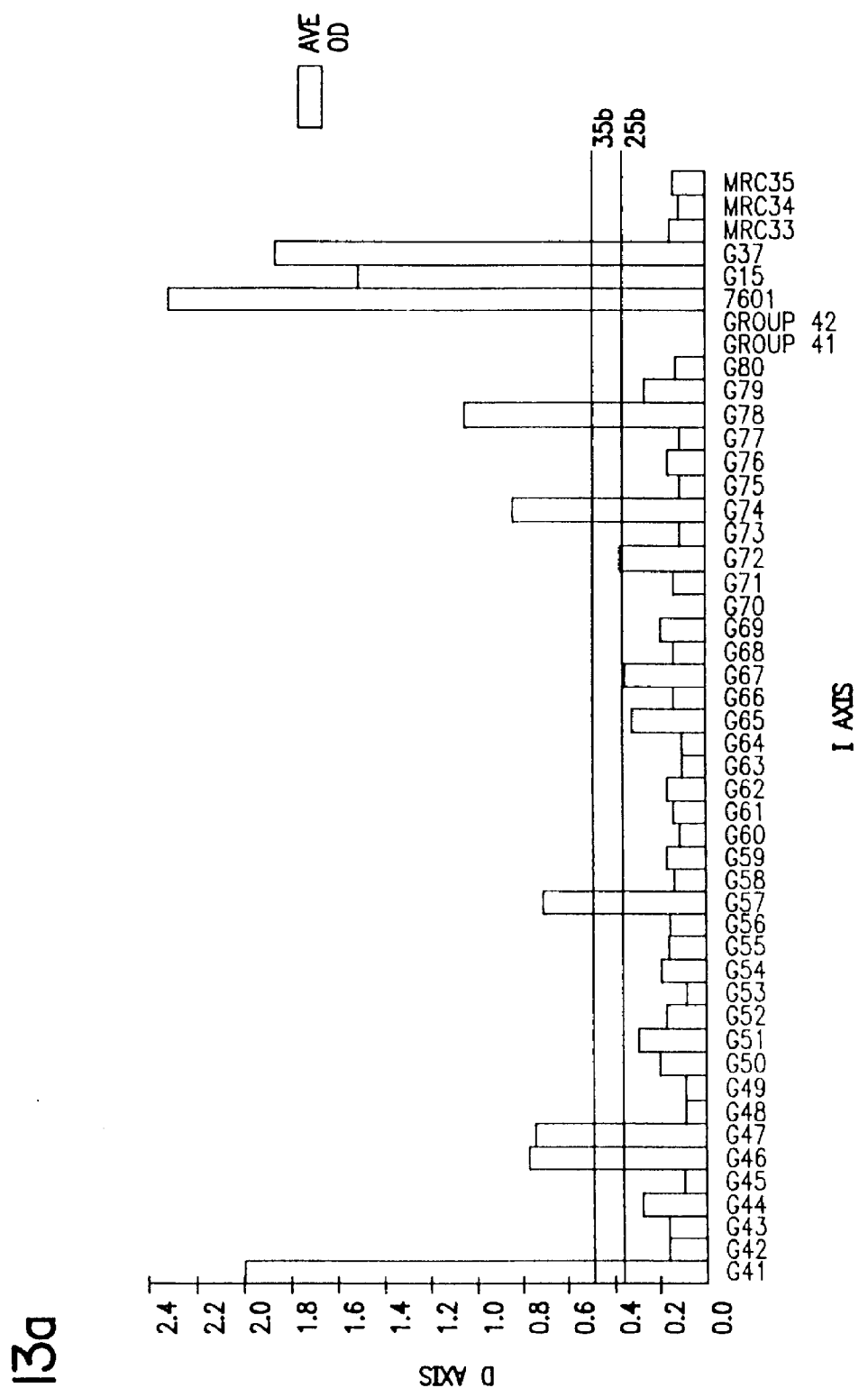
Figure 13B:
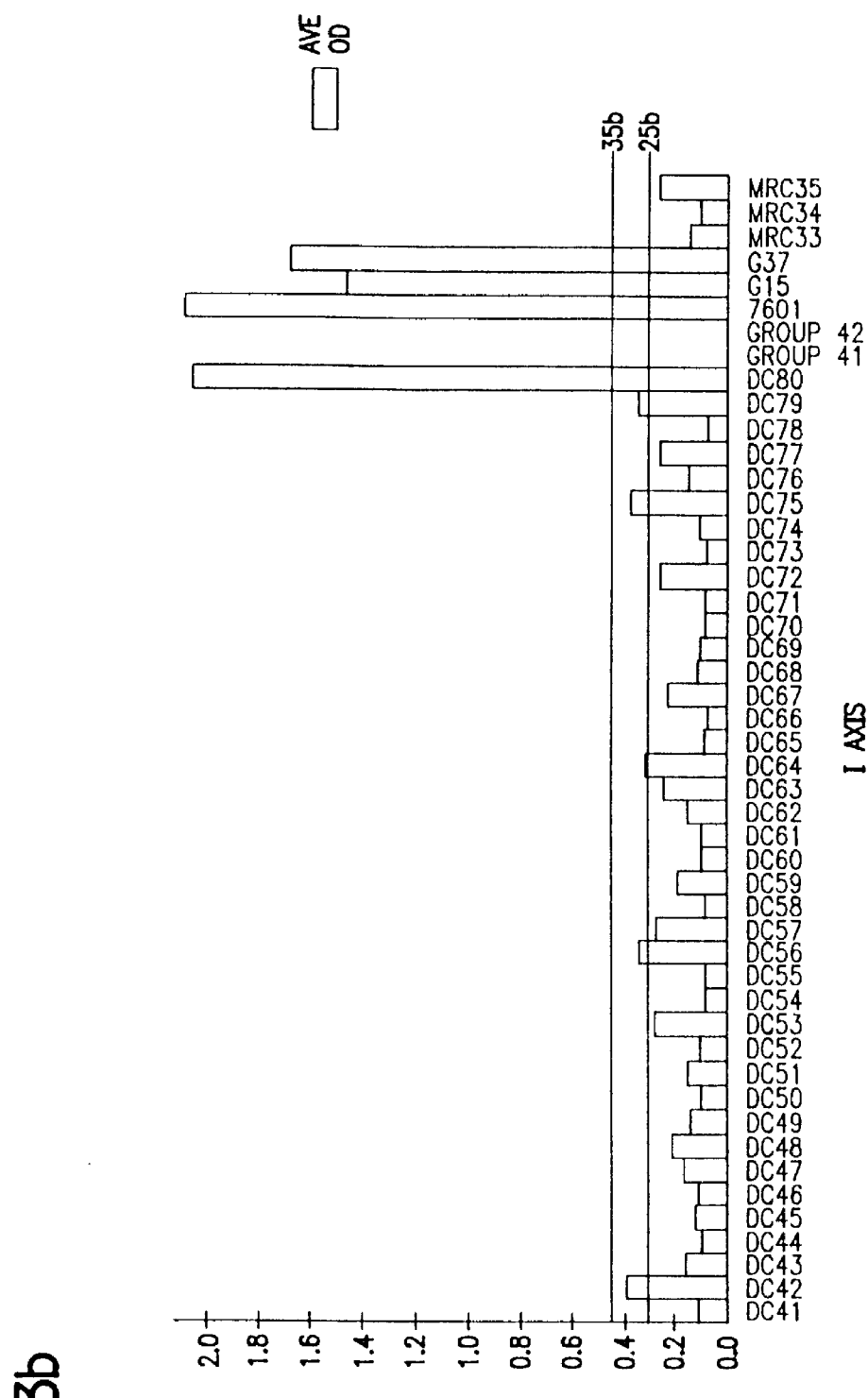

FIGS. 13A and 13B shows the reactivity of a panel of diabetic (G) and normal (DC) sera with ICA-12 in an ELISA format. The last 6 sera on the right side of the panel are controls. In this experiment, a capture format was used, in which an Immulon-1 plate (Dynatech) was coated first with a conjugate of glutathione and bovine serum albumin (GT-BSA). This conjugate was formed by reacting 2 mg of reduced glutathione (Sigma G-4251) dissolved in 500 μl PBS with 2 mg maleimide activated BSA (Pierce 77115H) dissolved in 200 μl water for 2 hours at room temperature. The mixture containing the modified BSA was diluted 1/1400 in EIA coating buffer (0.1M sodium carbonate, pH 9.5), and each well of the 96-well plate was coated with 50 μl overnight at room temperature. The plate was blocked as described above, washed, and each well was exposed to 300 ng GST-ICA-12 fusion protein dissolved in 50 μl blott/ Tween for 1 hour at room temperature. Incubation with human sera, washing, and development were done as described above.

The present invention has been particularly described and exemplified above. It is contemplated that many other variations and modifications of the invention can be made without departing from the spirit and scope hereof.

What is claimed is:

1. A non-glycosylated polypeptide comprising the sequence of amino acids encoded by the DNA insert of a recombinant cloning vehicle selected from the group consisting of ATCC 40550, 40551, 40552, 40553, 40554, 40703, 40704, 40705, 40706 and 75030.

2. A non-glycosylated polypeptide according to claim 1, which is obtained by expressing said DNA insert of said recombinant cloning vehicle in a bacterial cell.

3. A non-glycosylated polypeptide according to claim 1, which is obtained by peptide synthesis.

4. A non-glycosylated polypeptide according to claim 1, comprising the sequence of amino acids encoded by the DNA insert of recombinant cloning vehicle ATCC 40550.

5. A non-glycosylated polypeptide according to claim 1, comprising the sequence of amino acids encoded by the DNA insert of recombinant cloning vehicle ATCC 40551.

6. A non-glycosylated polypeptide according to claim 1, comprising the sequence of amino acids encoded by the DNA insert of recombinant cloning vehicle ATCC 40552.

7. A non-glycosylated polypeptide according to claim 1, comprising the sequence of amino acids encoded by the DNA insert of recombinant cloning vehicle ATCC 40553.

8. A non-glycosylated polypeptide according to claim 1, comprising the sequence of amino acids encoded by the DNA insert of recombinant cloning vehicle ATCC 40554.

9. A non-glycosylated polypeptide according to claim 1, comprising the sequence of amino acids encoded by the DNA insert of recombinant cloning vehicle ATCC 40703.

10. A non-glycosylated polypeptide according to claim 1, comprising the sequence of amino acids encoded by the DNA insert of recombinant cloning vehicle ATCC 40704.

11. A non-glycosylated polypeptide according to claim 1, comprising the sequence of amino acids encoded by the DNA insert of recombinant cloning vehicle ATCC 40705.

12. A non-glycosylated polypeptide according to claim 1, comprising the sequence of amino acids encoded by the DNA insert of recombinant cloning vehicle ATCC 40706.

13. A non-glycosylated polypeptide according to claim 1, comprising the sequence of amino acids encoded by the DNA insert of recombinant cloning vehicle ATCC 75030.

14. A fragment of a non-glycosylated polypeptide comprising the sequence of amino acids encoded by the DNA insert of a recombinant cloning vehicle selected from the group consisting of ATCC 40550, 40551, 40552, 40553, 40554, 40703, 40704, 40705, 40706 and 75030, said fragment being capable of binding an islet cell autoantibody.

15. A fragment of a non-glycosylated polypeptide according to claim 14, which is obtained by a process comprising expressing said DNA insert of said recombinant cloning vehicle in a bacterial cell.

16. A fragment of a non-glycosylated polypeptide according to claim 14, which is obtained by peptide synthesis.

17. A fragment of a non-glycosylated polypeptide according to claim 14, comprising the sequence of amino acids encoded by the DNA insert of recombinant cloning vehicle ATCC 40550, said fragment being capable of binding an islet cell autoantibody.

18. A fragment of a non-glycosylated polypeptide according to claim 14, comprising the sequence of amino acids encoded by the DNA insert of recombinant cloning vehicle ATCC 40551, said fragment being capable of binding an islet cell autoantibody.

19. A fragment of a non-glycosylated polypeptide according to claim 14, comprising the sequence of amino acids encoded by the DNA insert of recombinant cloning vehicle ATCC 40552, said fragment being capable of binding an islet cell autoantibody.

20. A fragment of a non-glycosylated polypeptide according to claim 14, comprising the sequence of amino acids encoded by the DNA insert of recombinant cloning vehicle ATCC 40553, said fragment being capable of binding an islet cell autoantibody.

21. A fragment of a non-glycosylated polypeptide according to claim 14, comprising the sequence of amino acids encoded by the DNA insert of recombinant cloning vehicle ATCC 40554, said fragment being capable of binding an islet cell autoantibody.

22. A fragment of a non-glycosylated polypeptide according to claim 14, comprising the sequence of amino acids encoded by the DNA insert of recombinant cloning vehicle ATCC 40703, said fragment being capable of binding an islet cell autoantibody.

23. A fragment of a non-glycosylated polypeptide according to claim 14, comprising the sequence of amino acids encoded by the DNA insert of recombinant cloning vehicle ATCC 40704, said fragment capable of binding an islet cell autoantibody.

24. A fragment of a non-glycosylated polypeptide according to claim 14, comprising the sequence of amino acids encoded by the DNA insert of recombinant cloning vehicle ATCC 40705, said fragment being capable of binding an islet cell autoantibody.

25. A fragment of a non-glycosylated polypeptide according to claim 14, comprising the sequence of amino acids encoded by the DNA insert of recombinant cloning vehicle ATCC 40706, said fragment being capable of binding an islet cell autoantibody.

26. A fragment of a non-glycosylated polypeptide according to claim 14, comprising the sequence of amino acids encoded by the DNA insert of recombinant cloning vehicle ATCC 75030, said fragment being capable of binding an islet cell autoantibody.

* * * * *

UNITED STATES PATENT AND TRADEMARK OFFICE
CERTIFICATE OF CORRECTION

PATENT NO. : 5,840,336
DATED     : November 24, 1998
INVENTOR(S) : Rabin, Daniel U.

It is certified that error appears in the above-identified patent and that said Letters Patent is hereby corrected as shown below:

Col. 64, line 32   After " fragment " insert -- being --

Signed and Sealed this

Twenty-third Day of November, 1999

Attest:

Q. TODD DICKINSON

Attesting Officer       Acting Commissioner of Patents and Trademarks